US009259283B2

United States Patent
Ogawa et al.

(10) Patent No.: US 9,259,283 B2
(45) Date of Patent: Feb. 16, 2016

(54) MEDICAL MASTER SLAVE MANIPULATOR SYSTEM

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 30 days.

(21) Appl. No.: 14/146,187

(22) Filed: Jan. 2, 2014

(65) Prior Publication Data
US 2014/0114481 A1  Apr. 24, 2014

Related U.S. Application Data

(63) Continuation of application No. PCT/JP2012/067876, filed on Jul. 6, 2012.

(30) Foreign Application Priority Data

Jul. 7, 2011 (JP) ................................. 2011-150977
Jul. 7, 2011 (JP) ................................. 2011-150978

(51) Int. Cl.
*G05B 19/18* (2006.01)
*A61B 19/00* (2006.01)

(52) U.S. Cl.
CPC ..... *A61B 19/2203* (2013.01); *A61B 2019/2223* (2013.01); *A61B 2019/5229* (2013.01); *A61B 2019/5255* (2013.01)

(58) Field of Classification Search
CPC ........ B25J 9/1664; B25J 9/1661; B25J 13/08; G05B 19/425; G05B 2219/45083

USPC ......................................................... 700/257
See application file for complete search history.

(56) References Cited

U.S. PATENT DOCUMENTS

D271,795 S  *  12/1983  Nakao ........................... D23/360
5,053,975 A     10/1991  Tsuchihashi et al.
5,876,325 A      3/1999  Mizuno et al.
(Continued)

FOREIGN PATENT DOCUMENTS

JP    63-150171 A    6/1988
JP    05-011713 A    1/1993
(Continued)

OTHER PUBLICATIONS

Extended Supplementary European Search Report dated Feb. 4, 2015 from related European Application No. 12 80 7156.0.
(Continued)

*Primary Examiner* — Ian Jen
(74) *Attorney, Agent, or Firm* — Scully, Scott, Murphy & Presser, PC

(57) ABSTRACT

A medical master slave manipulator system includes a master input device configured to send an operation command, a slave manipulator operated by the master input device, a control unit configured to transmit an operation signal to the slave manipulator based on the operation command, a display unit configured to display an image of an object, and an image selection device configured to select the image displayed on the display unit, wherein the control unit transforms the operation command associated with the image selected by the image selection device.

13 Claims, 20 Drawing Sheets

(56) References Cited

U.S. PATENT DOCUMENTS

| | | | |
|---|---|---|---|
| 6,167,292 A * | 12/2000 | Badano | A61B 19/54 600/407 |
| 6,424,885 B1 * | 7/2002 | Niemeyer | A61B 19/22 600/109 |
| 6,659,939 B2 | 12/2003 | Moll et al. | |
| 6,847,336 B1 * | 1/2005 | Lemelson | A61B 1/00048 345/8 |
| 7,607,440 B2 * | 10/2009 | Coste-Maniere | A61B 19/22 128/898 |
| 7,833,221 B2 * | 11/2010 | Voegele | A61B 17/3421 600/424 |
| 2002/0128552 A1 * | 9/2002 | Nowlin | A61B 19/22 600/427 |
| 2003/0230723 A1 * | 12/2003 | Garrard | G01T 1/1648 250/363.1 |
| 2005/0033117 A1 | 2/2005 | Ozaki et al. | |
| 2005/0228250 A1 * | 10/2005 | Bitter | A61B 5/02007 600/407 |
| 2006/0109237 A1 | 5/2006 | Morita et al. | |
| 2006/0274031 A1 * | 12/2006 | Yuen | H04N 7/144 345/156 |
| 2007/0043338 A1 * | 2/2007 | Moll | A61B 19/2203 606/1 |
| 2009/0036902 A1 * | 2/2009 | DiMaio | A61B 8/12 606/130 |
| 2009/0097612 A1 * | 4/2009 | Rauch | A61B 6/032 378/19 |
| 2009/0192519 A1 | 7/2009 | Omori | |
| 2009/0248036 A1 * | 10/2009 | Hoffman | A61B 19/2203 606/130 |
| 2009/0268015 A1 * | 10/2009 | Scott | A61B 1/00009 348/51 |

FOREIGN PATENT DOCUMENTS

| | | |
|---|---|---|
| JP | 05-301180 A | 11/1993 |
| JP | 07-328016 A | 12/1995 |
| JP | 08-154321 A | 6/1996 |
| JP | 08-155863 A | 6/1996 |
| JP | 08-223797 A | 8/1996 |
| JP | 08-275958 A | 10/1996 |
| JP | 08-309680 A | 11/1996 |
| JP | 2000-042960 A | 2/2000 |
| JP | 3482228 B2 | 12/2003 |
| JP | 2007-030136 A | 2/2007 |
| JP | 2008-228967 A | 10/2008 |
| JP | 2008-541990 A | 11/2008 |
| JP | 2009-045099 A | 3/2009 |
| JP | 2009-512514 A | 3/2009 |
| JP | 2009-178230 A | 8/2009 |
| JP | 2009-244949 A | 10/2009 |
| WO | WO 2007/030173 A1 | 3/2007 |
| WO | WO 2007/047782 A2 | 4/2007 |
| WO | WO 2010-151438 A | 12/2010 |

OTHER PUBLICATIONS

International Search Report dated Oct. 16, 2012 issued in PCT/JP2012/067876.

* cited by examiner

MEDICAL MASTER SLAVE MANIPULATOR SYSTEM

CROSS REFERENCE TO RELATED APPLICATIONS

This application claims priority of and the benefit of Japanese Patent Application No. 2011-150977 filed on Jul. 7, 2011, and Japanese Patent Application 2011-150978 filed on Jul. 7, 2011, and is a continuous application of international application PCT/JP2012/067876 filed on Jul. 6, 2012, the disclosures thereof are incorporated herein by reference.

BACKGROUND OF THE INVENTION

1. Field of the Invention

The present invention relates to a medical master slave manipulator system including a master input device and a slave arm.

2. Description of Related Art

In medical fields, a medical robot system (a medical master slave manipulator) including a master input device and a slave arm has been proposed. In a medical robot system disclosed in Japanese Unexamined Patent Application Publication (Translation of PCT Application) No. 2009-512514, a control switch mechanism for selecting the slave arm to control an actuation is installed at the master input device. In a first mode, a first slave arm is controlled by the master input device, and in a second mode, a second slave arm is controlled by the master input device. Which of the first slave arm and the second slave arm is controlled is switched by a control switch mechanism.

As the control switch mechanism, a voice command, a switch which is physically disposed, a foot pedal, icons or a graphic user interface selection device played on a display are taken.

In addition, in the medical robot system of Japanese Unexamined Patent Application Publication (Translation of PCT Application) No. 2009-512514, a control switch mechanism is installed separately from the above-mentioned mechanism. The control switch mechanism switches a mode for controlling an actuation by the master input device to an image capture mode for controlling a laparoscopic ultrasound (LUS) probe to acquire an auxiliary image, and an image operation mode for displaying and operating the auxiliary image on an original display image.

In the image operation mode, another auxiliary image such as an ultrasonography image or the like acquired by the LUS probe or the like is overlaid on an image of an endoscope or the like. Further, in the image operation mode, it is possible to allow the master input device to function as a pointing device.

SUMMARY OF THE INVENTION

According to a first aspect of the present invention, a medical master slave manipulator system includes a master input device configured to send an operation command; a slave manipulator operated by the master input device; a control unit configured to transmit an operation signal to the slave manipulator based on the operation command; a display unit configured to display an image of an object; and an image selection device configured to select the image displayed on the display unit, wherein the control unit transforms the operation command associated with the image selected by the image selection device.

According to a second aspect of the present invention, in the medical master slave manipulator system according to the first aspect of the present invention, a plurality of different images of the object may be displayed on the display unit, the image selection device may be configured such that an operator selects one image of the plurality of images, and the control unit may transform the operation command associated with the image selected by the operator via the image selection device.

According to a third aspect of the present invention, in the medical master slave manipulator system according to the second aspect of the present invention, the image selection device may include a detection unit configured to detect the image that a face of the operator is facing.

According to a fourth aspect of the present invention, in the medical master slave manipulator system according to the second aspect of the present invention, the image selection device may include an input portion configured to select the image selected by the operator.

According to a fifth aspect of the present invention, in the medical master slave manipulator system according to any one of the second to fourth aspects of the present invention, at least one of the plurality of images may be generated through image processing of another image.

According to a sixth aspect of the present invention, in the medical master slave manipulator system according to the fifth aspect of the present invention, at least one of the plurality of images may be generated through rotation processing of another image.

According to a seventh aspect of the present invention, in the medical master slave manipulator system according to the fifth aspect of the present invention, at least one of the plurality of images may be generated through scaling processing of another image.

According to an eighth aspect of the present invention, in the medical master slave manipulator system according to any one of the second to fourth aspects of the present invention, the plurality of images may be obtained by a plurality of different imaging devices, respectively.

According to a ninth aspect of the present invention, in the medical master slave manipulator system according to any one of the second to eighth aspects of the present invention, the master input device may include an input device, the slave manipulator may include a slave arm, the number of slave arms may be greater than the number of input devices, and in at least one of the transforming processings associated with the image, correspondence between the input device and the slave arm may be different from another transforming processing.

According to a tenth aspect of the present invention, the medical master slave manipulator system according to the eighth or ninth aspect of the present invention may include a plurality of the slave manipulators.

According to an eleventh aspect of the present invention, in the medical master slave manipulator system according to the first aspect of the present invention, the medical master slave manipulator system may further include an image processing unit configured to generate a first image signal according to the image of the object and a second image signal in which image processing is performed on the first image signal, wherein one of the first image signal and the second image signal is displayed on the display unit, the image selection device includes a switch unit configured to switch the image signal displayed on the display unit, and when the switch unit switches the image signal displayed on the display unit, the control unit transforms the operation command associated with the image signal displayed on the display unit.

According to a twelfth aspect of the present invention, in the medical master slave manipulator system according to the eleventh aspect of the present invention, the master input device may include an input device, the slave manipulator may include a slave arm, the number of slave arms is greater than the number of input devices, and correspondence between the input device and the slave arm may be different from another transforming processing in transforming processing associated with the first image signal and transforming processing associated with the second image signal.

According to a thirteenth aspect of the present invention, the medical master slave manipulator system according to the eleventh aspect of the present invention may further include an imaging device including a driving unit and configured to acquire the first image signal, wherein, as a predetermined update input is performed after driving the driving unit, contents of transforming processing associated with the first image signal and the first image signal are updated.

According to a fourteenth aspect of the present invention, in the medical master slave manipulator system according to the thirteenth aspect of the present invention, when the first image signal is updated, setting of the image processing may be updated such that substantially the same image as the image displayed on the display unit by the first image signal before being updated is displayed on the display unit.

DETAILED DESCRIPTION OF THE INVENTION

Figure 1:
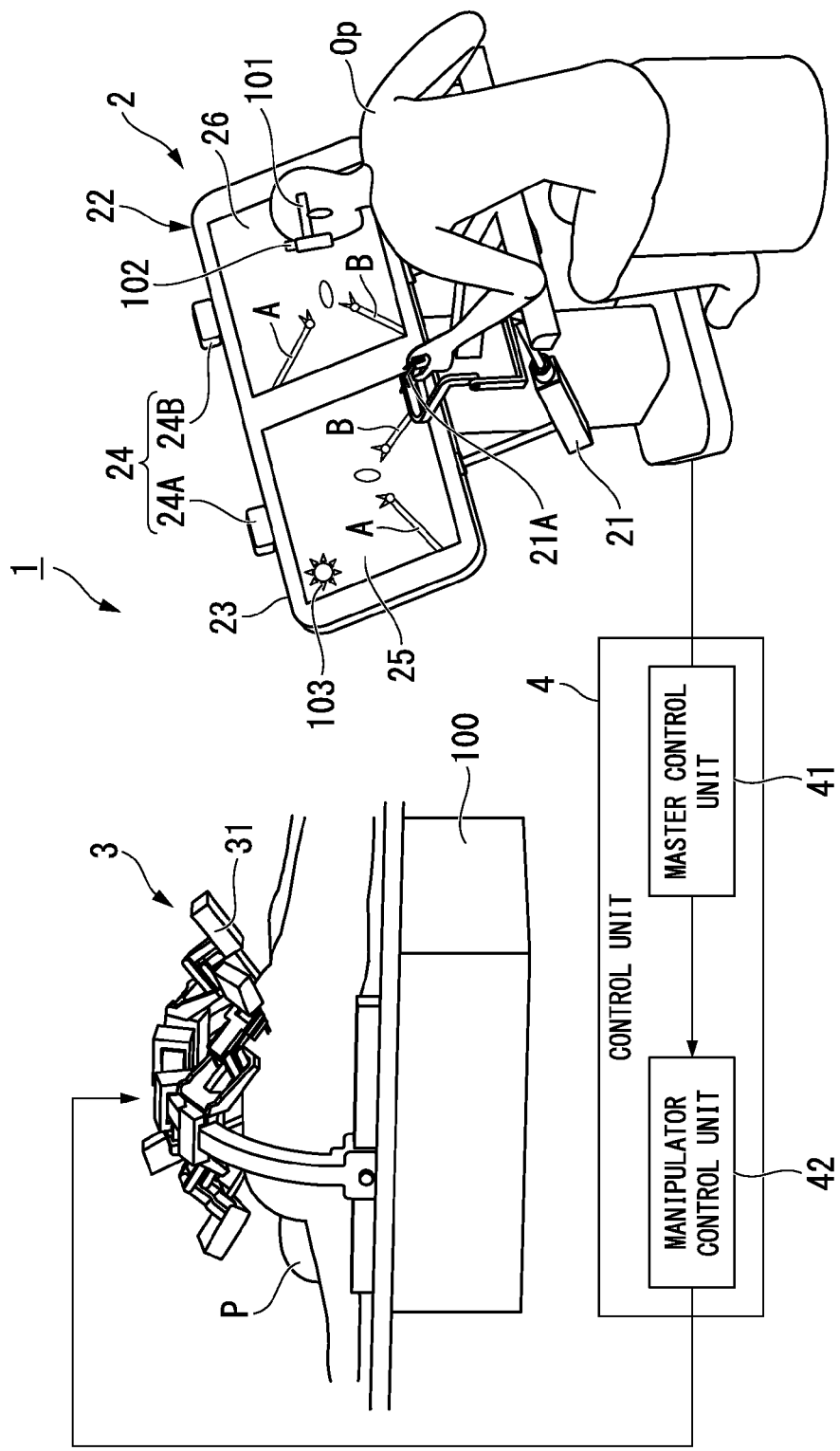
FIG. 1 is a diagram showing a medical manipulator system to which a medical master slave manipulator system according to a first embodiment of the present invention is applied.

Hereinafter, a first embodiment of the present invention will be described. FIG. 1 is a diagram showing a medical master slave manipulator system (hereinafter, simply referred to as "a master slave manipulator system") 1 of the present embodiment. The master slave manipulator 1 includes a master input device 2 having a master arm 21 and sending an operation command, and a slave manipulator 3 having a slave arm 31. The master slave manipulator 1 is a system that remotely controls the slave arm 31 so that the slave arm 31 follows an operation of the master arm 21 by an operator (surgeon) Op. The operation command via the master arm 21 is transmitted to a master control unit 41 of a control unit 4, and input into a manipulator control unit 42 after transforming processing, which is to be described, according to the necessity is performed. Thereafter, an actuation signal is transmitted from the manipulator control unit 42 to the slave manipulator 3 to actuate the slave arm 31.

As shown in FIG. 1, the slave manipulator 3 is installed at an operating table 100 on which a patient P is laid, and includes a plurality of slave arms 31. Each of the slave arms includes a plurality of joints with multiple degrees of freedom, and is configured to realize multiaxial actuation. Each of the joints with multiple degrees of freedom is individually driven by a power unit (not shown). As the power unit, for example, a motor (a servo motor) or the like having a servo mechanism provided with an incremental encoder or a speed reducer can be employed.

An imaging device (not shown) such as an endoscope configured to acquire a video of an operative field including an area to be manipulated (an object) is attached to one of the plurality of slave arms 31. A treatment instrument (not shown) configured to perform various treatments is attached to another slave arm. A well-known device can be appropriately selected and used as the imaging device or the treatment instrument. In addition, each of the slave arms also includes a plurality of power units (not shown) configured to drive the mounted treatment instrument or the like. A servo motor, for example, can also be used as the power unit. In addition, in the following description, among the slave arms, the slave arm to which the treatment instrument is attached may be referred to as "a slave arm for treatment."

The master input device 2 includes a plurality of master arms 21 operated by the operator Op, and a display unit 22 on which an image obtained by the imaging device is displayed. Each of the master arms 21 includes a well-known configuration enabling multiaxial actuation. Each of the master arms 21 includes a grip portion 21A formed at its distal end side adjacent to the operator Op and functions as an operation unit (an input device) gripped by the operator to send an operation command.

The display unit 22 includes a display 23 on which an image is displayed, and a detection unit (an image selection device) 24 attached to the display 23 and configured to detect a direction of the face of the operator.

The display 23 has two screens, a first screen 25 and a second screen 26. An image of an operative field obtained by the imaging device is displayed on the first screen 25. An image of the operative field (hereinafter referred to as "a rotational operative field image") in which the image is rotated to a predetermined rotation angle (for example, 90 degrees) is displayed on the second screen 26. In the present embodiment, the two images having an error corresponding to a parallax are projected to the screens 25 and 26. The operator Op can three-dimensionally view the image of each of the screens 25 and 26 through well-known 3D glasses 101 including a polarization mechanism or a shutter mechanism.

The detection unit 24 includes a first detection unit 24A installed at an upper side of the first screen 25, and a second detection unit 24B installed at an upper side of the second screen. Each of the detection units 24A and 24B includes a light receiving element. Each of the detection units 24A and 24B receives light emitted from a light emitting unit 102 attached to the 3D glasses 101 to detect the direction of the face of the operator Op.

In addition, a configuration of the detection unit is not limited to the above-mentioned configuration but various well-known mechanisms can be appropriately selected and employed. The detection unit may be configured not to use light reception and emission as a detection principle. The detection unit may be configured to acquire, for example, an image of the face or an eyeball of the operator to detect a direction of a line of sight from the image.

Figure 2:
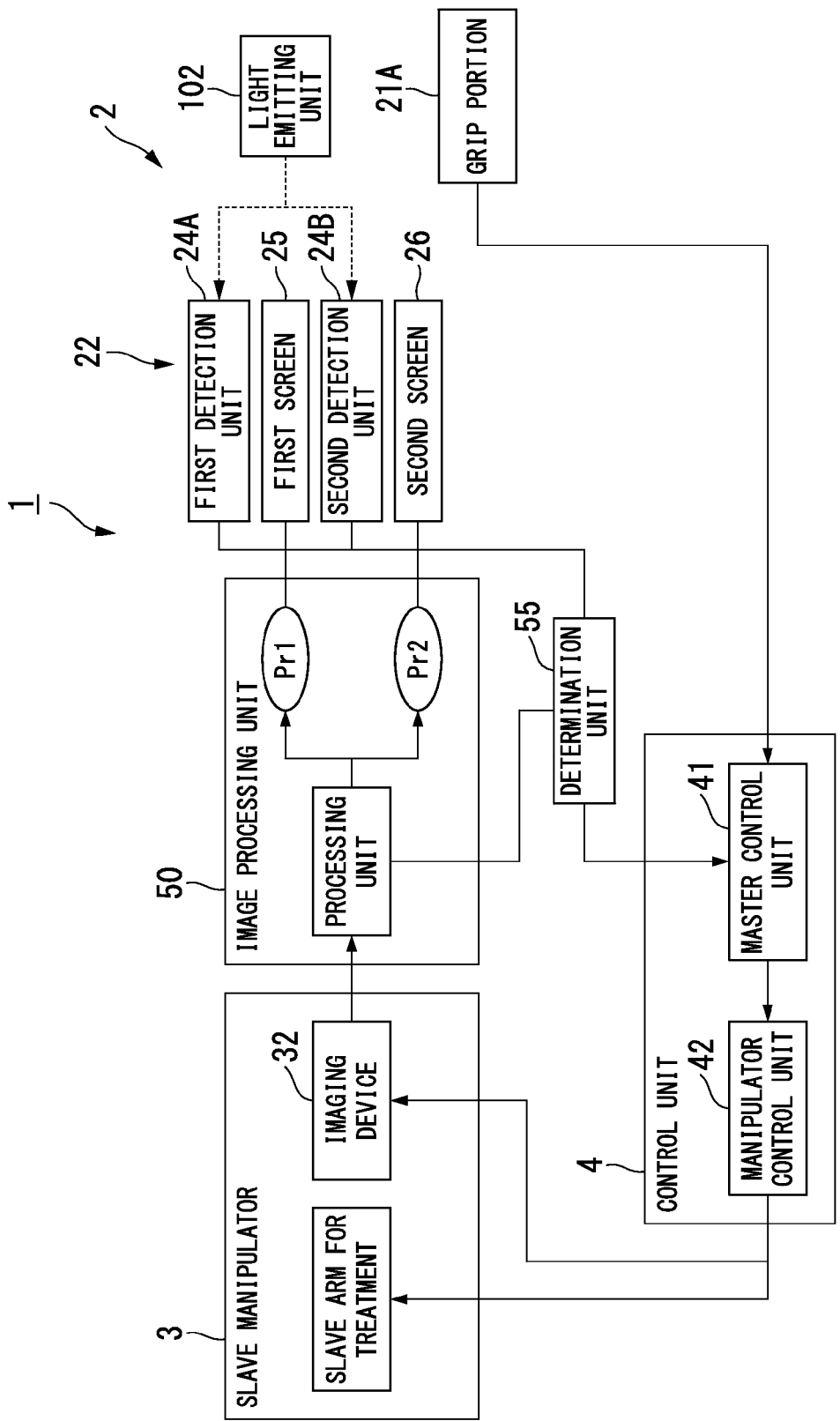
FIG. 2 is a functional block diagram of the medical master slave manipulator system according to the first embodiment of the present invention.

FIG. 2 is a functional block diagram of the master slave manipulator 1. An image processing unit 50 is installed between an imaging device 32 and the display unit 22. The image processing unit 50 is a well-known processing circuit or processing program. An image signal transmitted from the imaging device 32 is processed in the image processing unit 50 in a state in which the image can be displayed. The processed signal is displayed on the first screen 25 of the display unit 22 via first transforming processing Pr1, and displayed on the second screen 26 via second transforming processing Pr2. In the present embodiment, the image acquired by the imaging device 32 is displayed on the first screen 25 as it is, and the image in which the image acquired by the imaging device 32 is rotated 90 degrees rightward is displayed on the second screen 26. That is, the second transforming processing Pr2 is processing of rotating the image 90 degrees rightward, and the first transforming processing Pr1 is transforming processing, which is referred to as "non-transforming." In the present embodiment, the "non-transforming" is also defined as one of the transforming processings.

In addition, a switched image rotated by image processing maintains a 3D display that can be recognized by the operator after being switched. For example, while two images corresponding to binocular disparity are displayed on the same screen in the 3D display, the two images are re-transformed to maintain the 3D display in consideration of the binocular disparity corresponding to a rotation amount upon the image processing, and are displayed on the display unit 22.

A determination unit 55 is installed between the detection unit 24 and the master control unit 41. The determination unit 55 determines whether the face of the operator Op is facing any one of the screens 25 and 26 of the display 23 or not facing any one of the screens based on information transmitted from the detection unit 24, and transmits the determination result to the master control unit 41.

The actuation of the master slave manipulator 1 configured as described above will be described.

Figure 3:
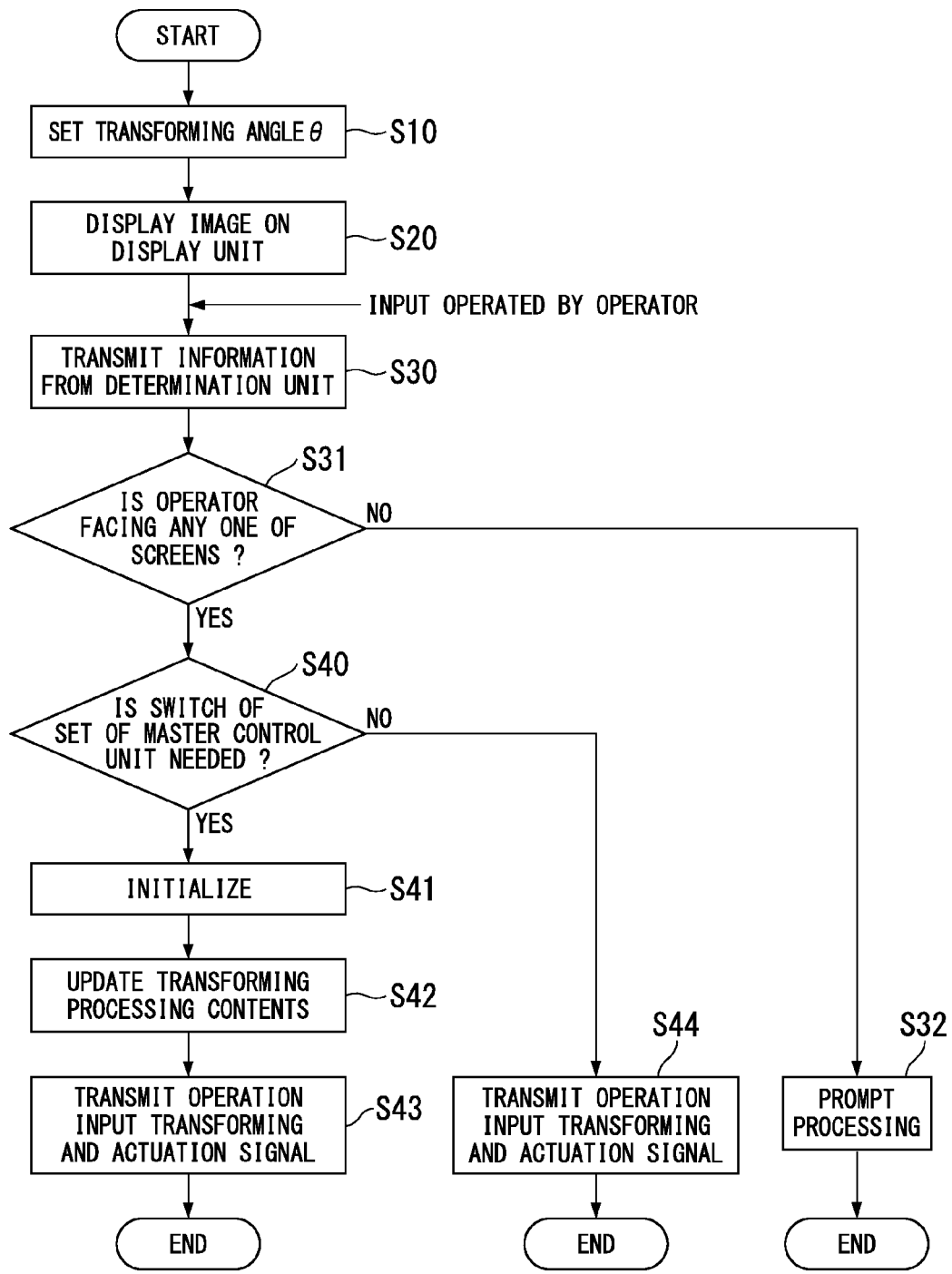
FIG. 3 is a flowchart showing a flow of actuations of the medical master slave manipulator system according to the first embodiment of the present invention.

FIG. 3 is a flowchart showing a flow of actuations of the master slave manipulator 1.

First, in step S10, the operator Op inputs a rotation angle θ (for example, 90 degrees rightward) of a rotational operative field image displayed on the second screen 26 into the image processing unit 50 via an interface (not shown) of the master input device, and sets a transforming angle θ to generate the image displayed on the second screen.

When the image signal is transmitted from the imaging device 32, in step S20, the image processing unit 50 performs the first image processing Pr1 with respect to the image signal and then, displays the image signal on the first screen 25. Further, simultaneously, the image processing unit 50 performs the second image processing Pr2 to the same image signal and then, displays the image signal on the second screen 26. Accordingly, in the image acquired by the imaging device 32 being displayed on the first screen 25 as it is, and in the image in which the image acquired by the imaging device 32 is rotated by a rotation angle θ being displayed on the second screen 26, the image is displayed on the display unit 22. The processing and the display of the image by the image processing unit 50 are continued while the image signal is transmitted from the imaging device 32.

During the actuation of the master slave manipulator 1, the determination unit 55 determines again whether the face of the operator is facing any one screen of the display unit 22 or not facing any one, based on the information received from the detection unit 24.

Figure 4:
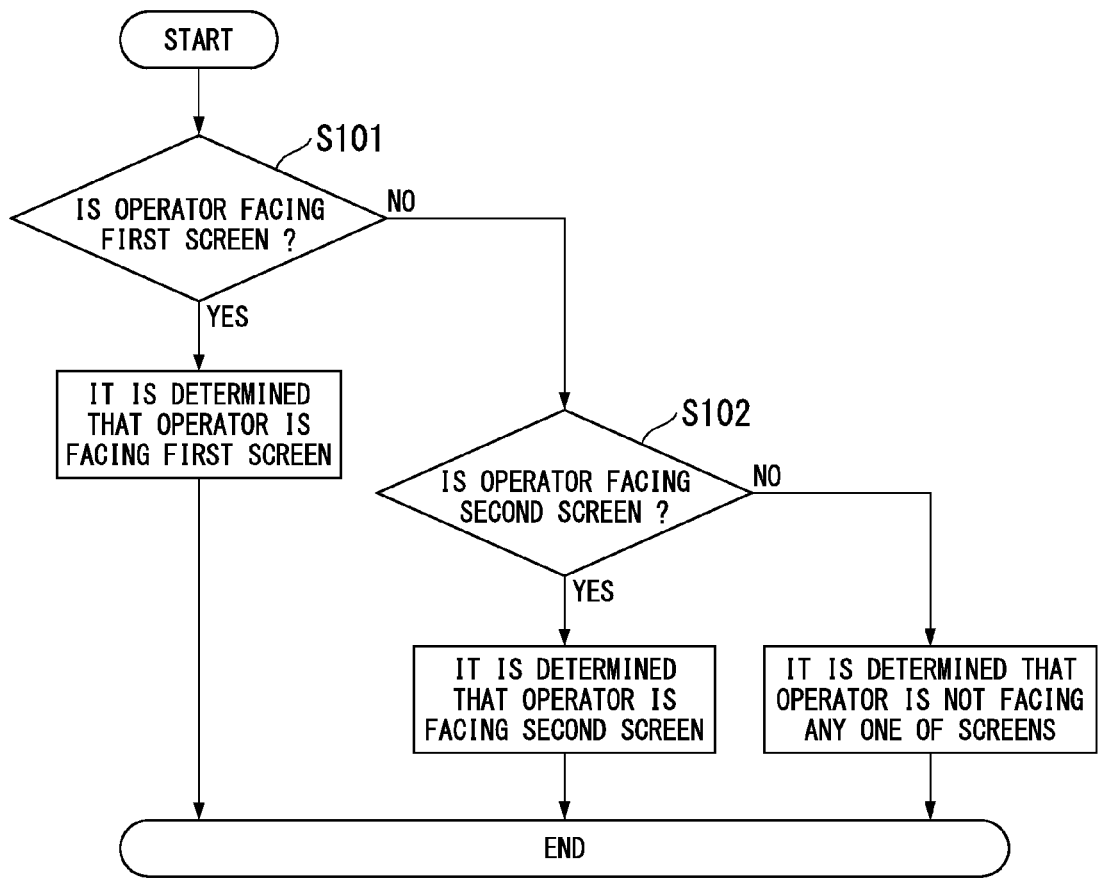
FIG. 4 is a flowchart showing a determination routine in a determination unit of the medical master slave manipulator system according to the first embodiment of the present invention.

FIG. 4 is a flowchart showing a determination routine of the determination unit 55. In step S101, based on the information transmitted from the first detection unit 24A, it is determined whether the face of the operator is facing the first screen 25 or not. When the determination in step S101 is Yes, the determination unit 55 determines that the operator is facing the first screen 25, that is, the operator selects the image displayed on the first screen 25, and terminates the processing. When the determination in step S101 is No, step S102 is performed.

In step S102, based on the information transmitted from the second detection unit 24B, it is determined whether the operator is facing the second screen 26 or not. When the determination in step S102 is Yes, the determination unit 55 determines that the face of the operator is facing the second screen 26, that is, the operator selects the image displayed on the second screen 26, and terminates the processing. When the determination in step S102 is No, it is determined that the operator is not facing any one of the first screen 25 and the second screen 26, and the processing is terminated.

In addition, when it is determined that the operator is facing any one of the first screen 25 and the second screen 26, the determination unit 55 transmits that information to the image processing unit 50. The image processing unit 50 in which the information is received displays a marker 103 (see FIG. 1) on the screen that it is determined that the operator is facing, and assists recognition of the operator. Here, the marker is not limited to the display on the screen, but an emission indicator such as an LED may be installed at an upper portion of the screen to assist recognition of the operator through lighting.

Returning to FIG. 3, when the operator sends an operation command to the grip portion 21A of the master input device 2, in step S30, inquiry to the determination unit 55 about the screen that the operator Op is facing is performed from the master control unit 41 in which the input is received. Then, the information is transmitted from the determination unit 55 to the master control unit 41 based on determination contents of the determination unit 55 at that time. Here, the information including the determination contents based on the above-mentioned determination routine and transforming processing contents of the operation command by the master control unit 41 associated with the determination contents are transmitted from the determination unit 55.

Next, in step S31, it is verified whether the operator faces any one of the first screen 25 and the second screen 26 based on the information transmitted from the determination unit 55. When the determination result is Yes, the processing goes to step S40. When the determination result is No, the processing goes to step S32.

In step S32, the information showing that the operator is not facing any one of the first screen 25 and the second screen 26 is transmitted from the determination unit 55 to the image processing unit 50, and the processing of prompting the operator Op is performed. For example, information such as "Please face the screen," "Please wear the 3D glasses," or the like, is displayed on the display unit 22. Then, at this time, with respect to the operation command from the master input device 2, the actuation of the slave manipulator 3 may be stopped.

In step S40, whether a switch in setting of the master control unit 41 is needed or not is determined.

For example, while the master control unit 41 performs the transforming processing of the operation command corresponding to the first screen 25, when the information showing "the operator Op is facing the second screen 26" is transmitted from the determination unit 55, since the switch in setting of the master control unit 41 is needed, the determination result becomes Yes, and the processing goes to step S41.

In step S41, the master control unit 41 performs initialization to match a position and an orientation of the grip portion 21A of the master input device 2 to a position and an orientation of a distal end of the slave arm 31 for treatment in the image displayed on the second screen 26 based on the information received from the determination unit 55. The master control unit 41 calculates a difference between the position and orientation of the grip portion 21A and the position and orientation of the distal end of the slave arm 31 for treatment in the second screen 26, and actuates a driving unit of the master input device 2 such that the difference becomes zero, performing the initialization of the grip portion 21A. At this time, a message such as "Initialization is in process. Please keep hands away from the grip portion," or the like, is displayed on the display unit 22 to prompt the operator.

In addition, the "positions" of the master arm and the slave arm are three-dimensional positions represented in an XYZ coordinate system of predetermined areas of the master arm and the slave arm (for example, the grip portion 21A, a distal end of the treatment instrument, and so on). The "orientation" of the master arm and the slave arm means a direction of the distal end with respect to the predetermined area as a reference point. In addition, in the master slave manipulator, position alignment and orientation alignment are well-known in the art, and a specific method thereof is not limited thereto.

Next, in step S42, the contents of the transforming processing of the operation command in the master control unit 41 are updated by the information from the determination unit 55. Accordingly, the master control unit 41 transformes the operation command such that an actuation direction of the grip portion 21A coincides with an actuation direction of the distal end of the slave arm 31 for treatment in the image selected by the operator Op. After the transforming processing contents are updated, in step S43, the master control unit 41 transforms the operation command associated with the screen selected by the operator Op, and transmits an actuation signal to the manipulator control unit 42. Then, the processing is terminated.

When the information of the determination unit 55 coincides with the setting of the master control unit 41, the determination result becomes No, and the processing goes to step S44. In step S44, the master control unit 41 performs the transforming processing of the operation command with the setting at that time to transmit the actuation signal to the manipulator control unit 42. Then, the processing is terminated.

According to the master slave manipulator 1 of the present embodiment, whether the face of the operator Op is facing any one of the screens 25 and 26 of the display unit 22 is determined by the determination unit 55 based on the information of the detection unit 24. Then, based on the determination result, the contents of the transforming processing are updated to transform the operation command associated with the image selected by the master control unit 41 such that the moving direction of the distal end of the slave arm 31 for treatment in the image selected by the operator Op is identical to the moving direction of the grip portion 21A. Accordingly, as the operator is merely facing the screen appropriate for the manipulation or operation to be performed, the contents of the transforming processing of the master control unit are automatically adjusted. As a result, the operator can intuitively operate the grip portion while looking at the screen, and intuitively operate the slave manipulator with no stress.

In addition, when the contents of the transforming processing of the master control unit 41 are updated, the initialization of the position and orientation of the grip portion 21A is performed. For this reason, as well as the actuation direction of the grip portion 21A, the position and orientation relation can also automatically be matched with the distal end of the slave arm 31 for treatment. Accordingly, the operator can more intuitively perform the operation.

Further, the rotational operative field image displayed on the second screen 26 is generated by performing the image processing with respect to the image obtained by the imaging device 32. For this reason, since the operator Op performs the manipulation at different points of view, there is no need to drive the imaging device 32. Accordingly, the operator can immediately switch the point of view of the operative field, and a series of manipulations can be smoothly performed. Furthermore, since interference with another slave arm due to driving of the imaging device can be prevented, reliability of the manipulation is improved.

In addition, the first screen 25 and the second screen 26 are displayed in parallel. For this reason, the operator Op can visually and approximately confirm the other screen with peripheral vision while looking at the one screen and performing the manipulation. Accordingly, the operator can perform a determination that the other confirmed screen is in a manipulator disposition from which it is easy to perform the manipulation during the manipulation, and when the operator is facing the other screen as needed, it is possible to smoothly switch the screen used for the manipulation, intuitively continue the manipulation regardless of a coordinate displacement after the switching.

In the present embodiment, while an example in which the master control unit 41 drives the master input device 2 to perform the initialization has been described, instead of this, the operator may perform the initialization with manual operations. For example, the driving unit is not installed at the master input device, a foot switch for switching On/Off of transmission of the operation command from the master input device to the master control unit is installed. Then, a configuration in which the operator moves the grip portion to a desired position intended as an initial position while pushing the foot switch and pushes down again the foot switch to terminate the initialization may be provided. In this case, the position and orientation of the grip portion may not be entirely matched with the position and orientation of the distal end of the slave arm. However, since the slave arm is operated based on a difference of a movement from the initial position and a priority of the initial position set by the operator, the operator can intuitively perform the operation at the setting in which the operator can most easily operate.

A second embodiment of the present invention will be described with reference to FIGS. 5 and 6. The master slave manipulator 61 of the present embodiment is distinguished from the above-mentioned master slave manipulator 1 in that, when the screen, which is gazed, is switched, a corresponding relation between the master arm and the slave arm is switched. In addition, in the following description, same elements in the above description are designated by like reference numerals, and a description thereof will be omitted.

Figure 5:
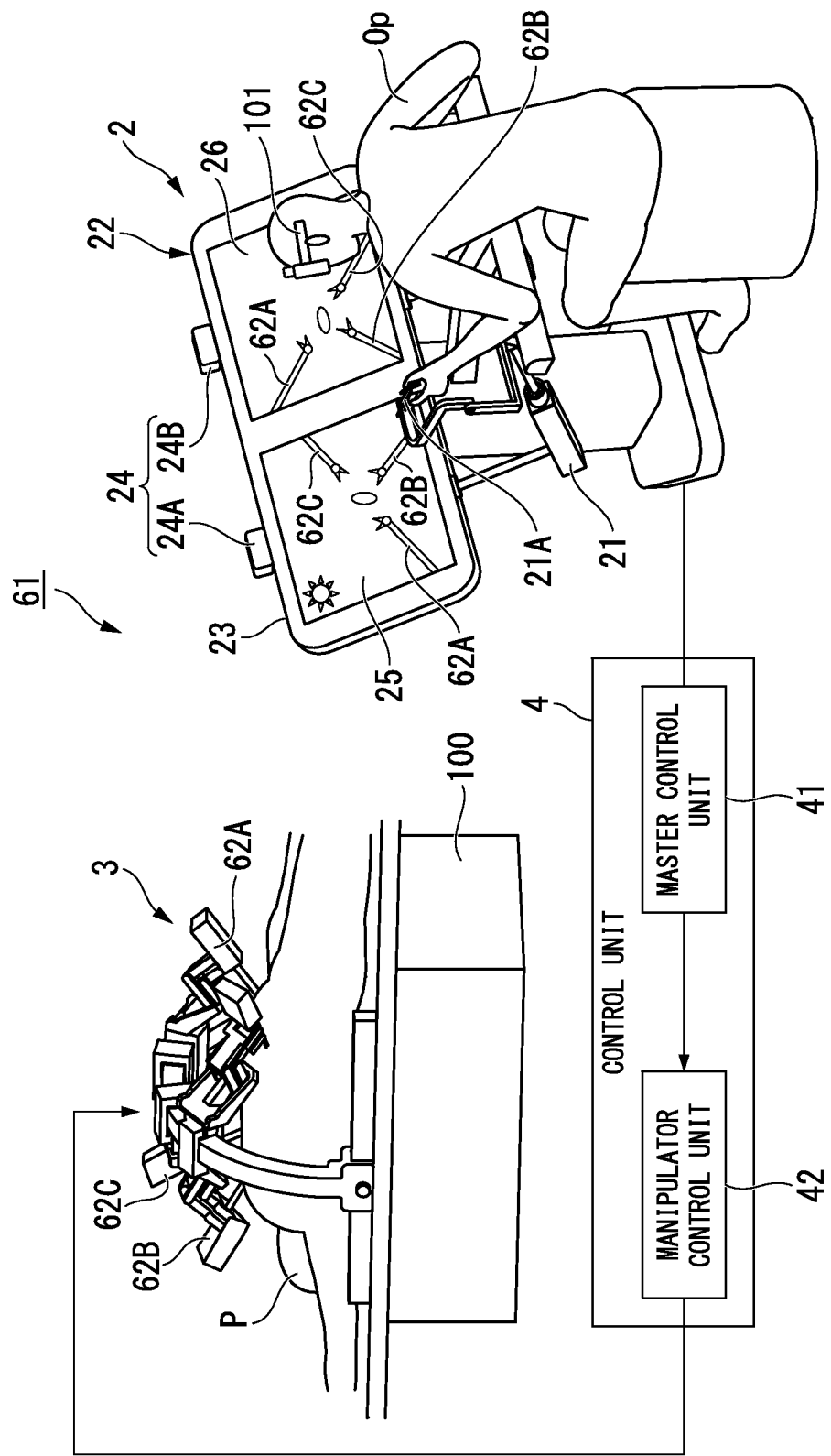
FIG. 5 is a diagram showing a medical manipulator system to which a medical master slave manipulator system according to a second embodiment of the present invention is applied.

FIG. 5 is a diagram showing the master input device 2 of the master slave manipulator 61. As shown in the display 23, three slave arms 62A, 62B and 62C for treatment are installed at the slave manipulator 3. On the first screen 25, the slave arms 62A and 62B are disposed at a position at which the operator Op can easily and intuitively perform the operation. On the second screen 26 rotated 90 degrees rightward, the slave arms 62B and 62C are disposed at a position at which the operator Op can easily and intuitively perform the operation. Only two master arms are installed at the master input device 2. For this reason, in the present embodiment, in each screen, two slave arms for treatment, which are easily and intuitively operated, are associated with the master arm. That is, correspondence relation between the master arm and the slave arm for treatment is varied according to the image displayed on each screen.

Figure 6:
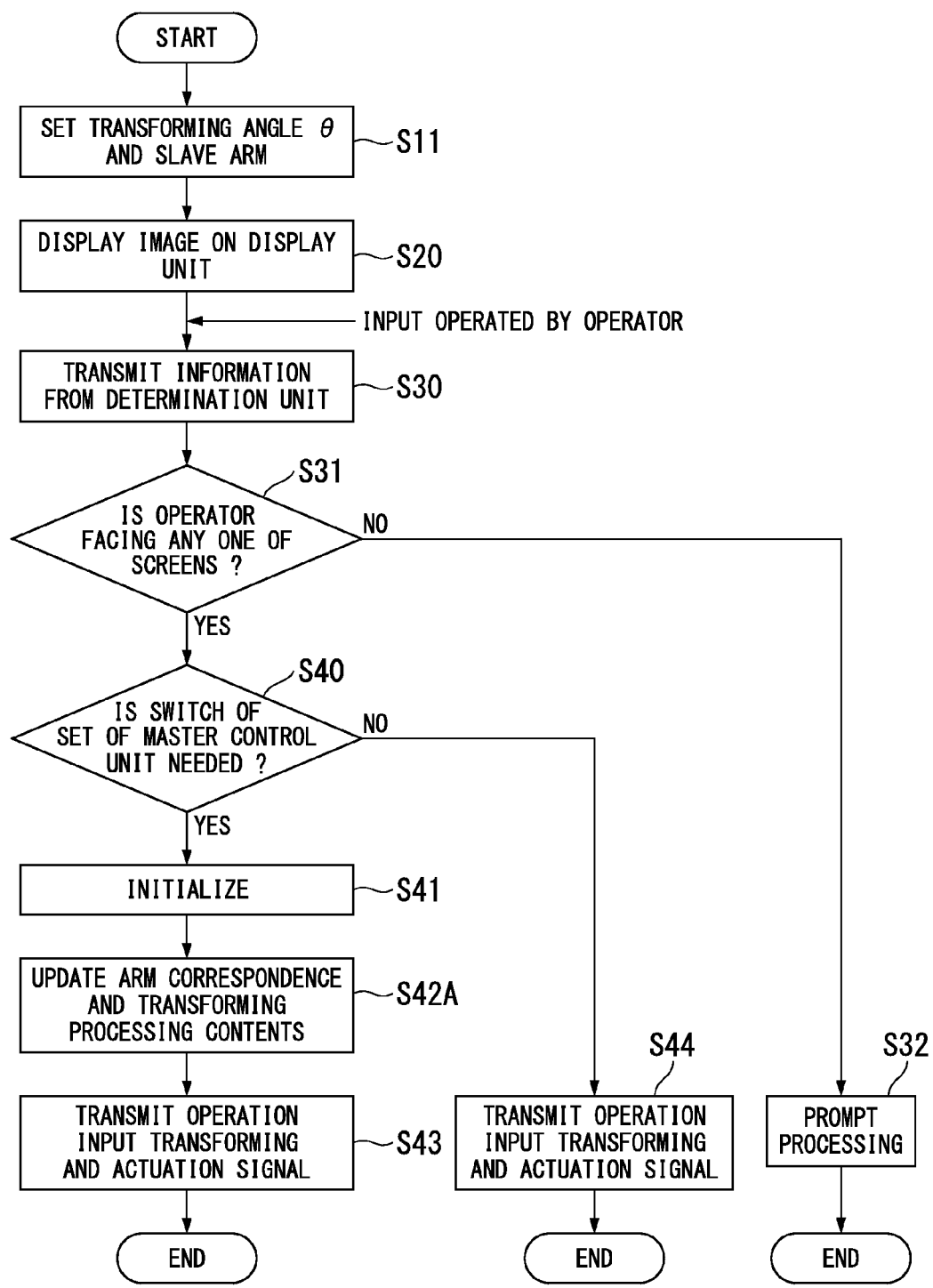
FIG. 6 is a flowchart showing a flow of actuations of the medical master slave manipulator system according to the second embodiment of the present invention.

FIG. 6 is a flowchart showing a flow of actuations of a master slave manipulator 61. In step S11, similar to the first embodiment, a conversion angle θ for generating a second screen is set by the operator Op. Further, two slave arms for treatment operated by the master arm 21 are set to the first screen 25 and the second screen 26, respectively.

Thereafter, in step S41, the initialization is performed such that the position and orientation between the distal ends of the two slave arms set in step S11 and the grip portion 21A of the master input device are matched with each other. Next, in step S42A, correspondence relation between the master arm and the slave arm and contents of the transforming processing of the operation command are updated.

Configurations other than those described above are basically same as the first embodiment.

Even in the master slave manipulator 61 of the embodiment, as the operator is merely facing the screen more appropriate for the manipulation or operation to be performed, the contents of the transforming processing of the master control unit can be automatically updated, and the operator can intuitively operate the master arm while looking at the screen to operate the slave arm with no stress.

Further, since the correspondence between the master arm and the slave arm are automatically updated, in each screen, the optimal slave arm can be operated to perform the manipulation.

In the embodiment, an example in which three slave arms for treatment are installed has been described. However, two slave arms for treatment may be installed. In addition, four or more slave arms for treatment may be installed. Further, instead of setting the transforming angle θ and the slave arm operated in each screen in step S11, a configuration in which the master control unit or the like automatically calculates a rotation angle, at which two slave arms having a different combination from the first screen are easily operated, to determine the transforming angle θ, based on the positional relation between the imaging device and each slave arm for treatment, may be provided. Here, the positional relation between the imaging device and each slave arm for treatment may be calculated from the image acquired by the imaging device, and may be calculated from the position information based on a value or the like of an encoder of the slave arm.

In addition, optimal correspondence between the slave arm and the master arm may be automatically calculated from the transforming angle θ initially determined in step S11, on the basis of positional relation information between the imaging device and the slave arm. Even in this case, similar to the above, the positional relation between the imaging device and each slave arm may be calculated from the image acquired by the imaging device, and may be calculated from the position information based on the value of the encoder of the slave arm.

As an another method, the correspondence between the slave arm and the master arm may be selected by the operator after step S40. A selecting method can be performed by an input switch such as an interface or the like.

A third embodiment of the present invention will be described with reference to FIGS. 7 to 9. A master slave manipulator 71 of the present embodiment is distinguished from the above-mentioned master slave manipulator 1 in that a plurality of slave manipulators are provided, and when the grazed screen is switched, the correspondence relation between the master arm and the slave manipulators is switched.

Figure 7:
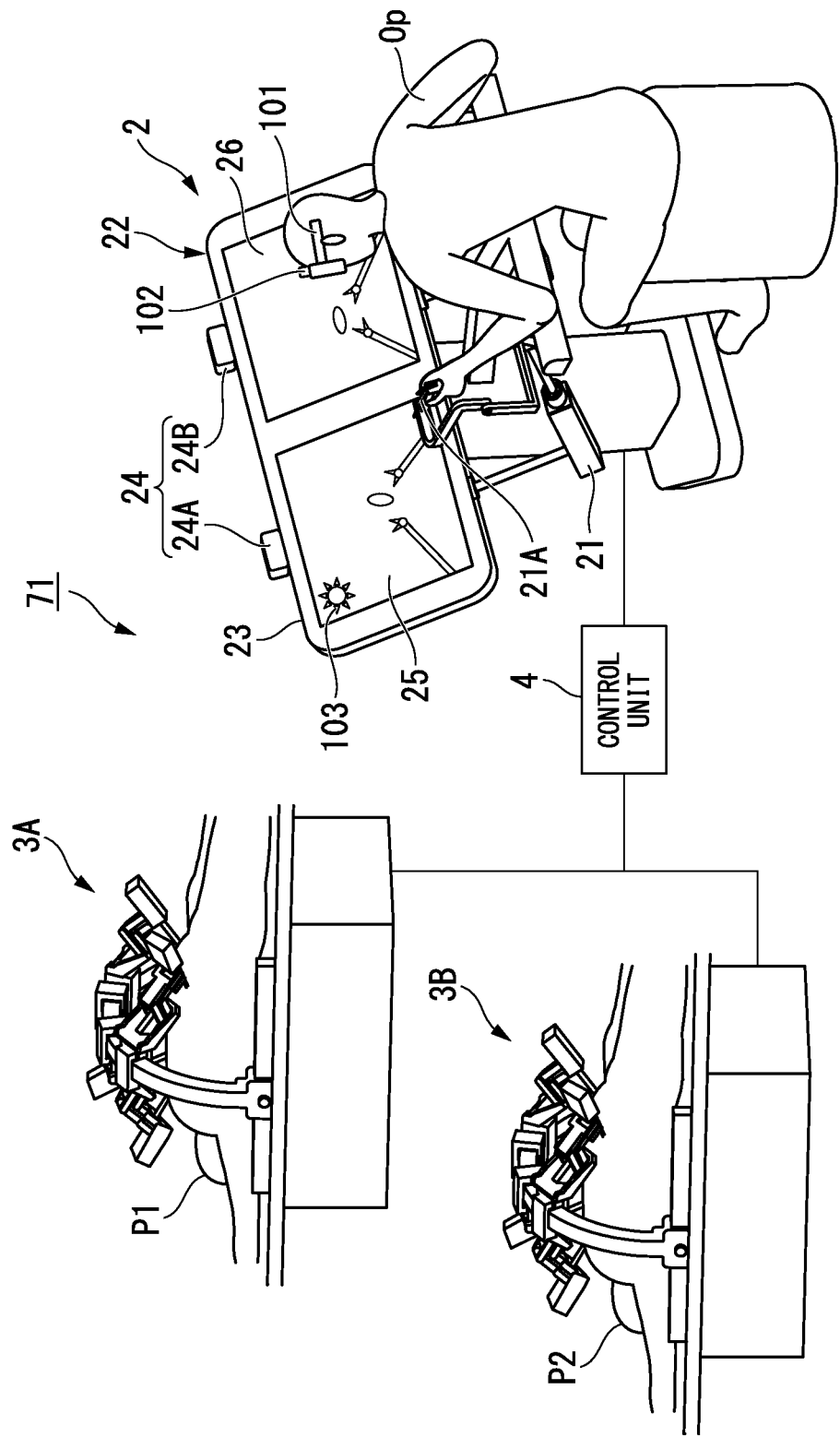
FIG. 7 is a diagram showing a medical manipulator system to which a medical master slave manipulator system according to a third embodiment of the present invention is applied.

FIG. 7 is a diagram showing the entire configuration of the master slave manipulator 71. The master slave manipulator 71 includes two slave manipulators designated by reference numerals 3A and 3B. The master slave manipulator 71 can simultaneously perform manipulations with respect to two patients P1 and P2. In addition, the patients are not limited to two, but two slave manipulators can be disposed with respect to different diseased parts of one patient.

Figure 8:
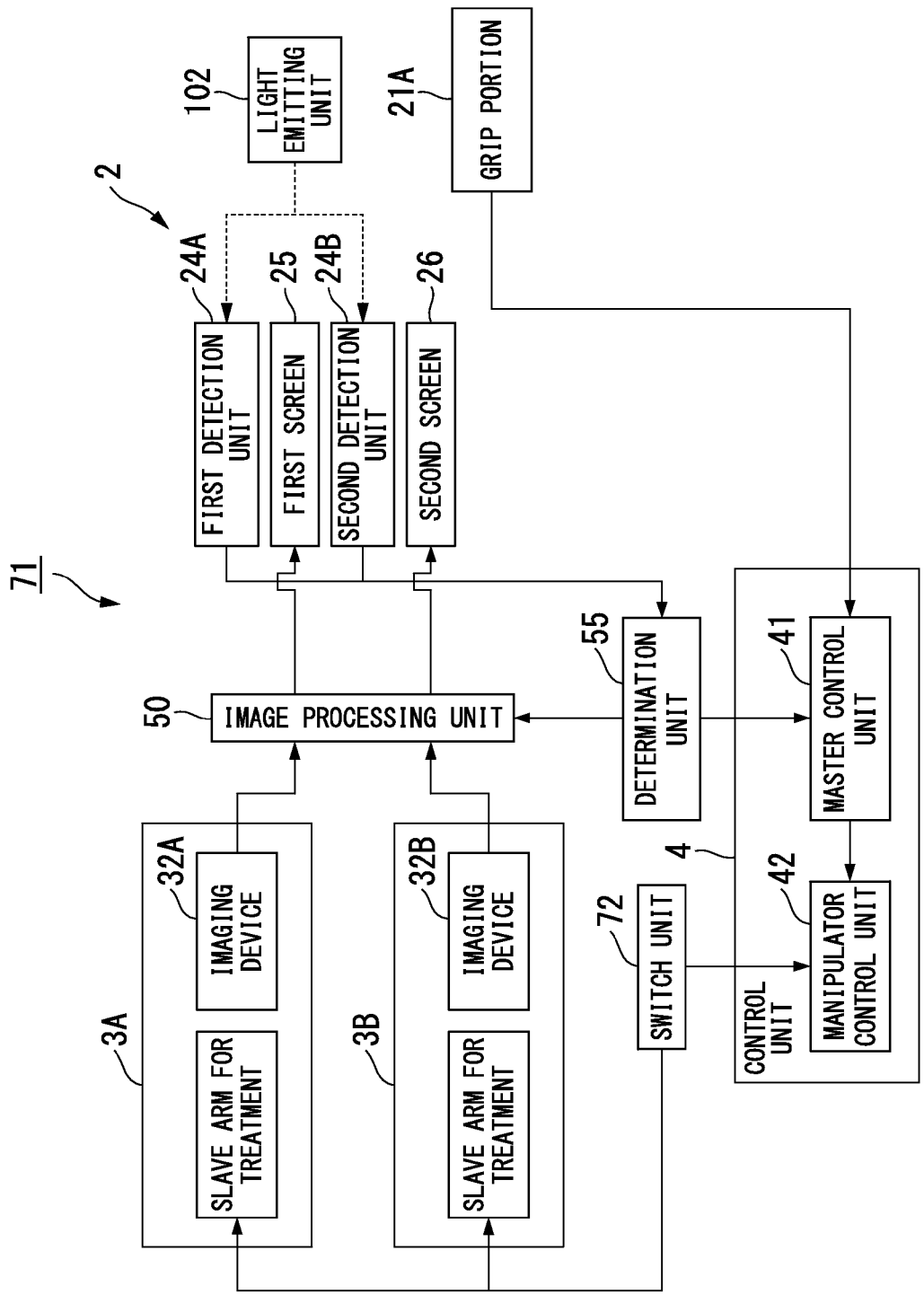
FIG. 8 is a functional block diagram of the medical master slave manipulator system according to the third embodiment of the present invention.

FIG. 8 is a functional block diagram of the master slave manipulator 71. The slave manipulators 3A and 3B have imaging devices 32A and 32B, respectively. An image acquired by the imaging device 32A is displayed on the first screen 25. An image acquired by the imaging device 32B is displayed on the second screen 26.

A switch unit 72 is installed between the manipulator control unit 42 and the slave manipulators 3A and 3B. The manipulator control unit 42 is selectively connected to one of the slave manipulators 3A and 3B, and the operation signal from the manipulator control unit is transmitted to the connected slave manipulator.

Figure 9:
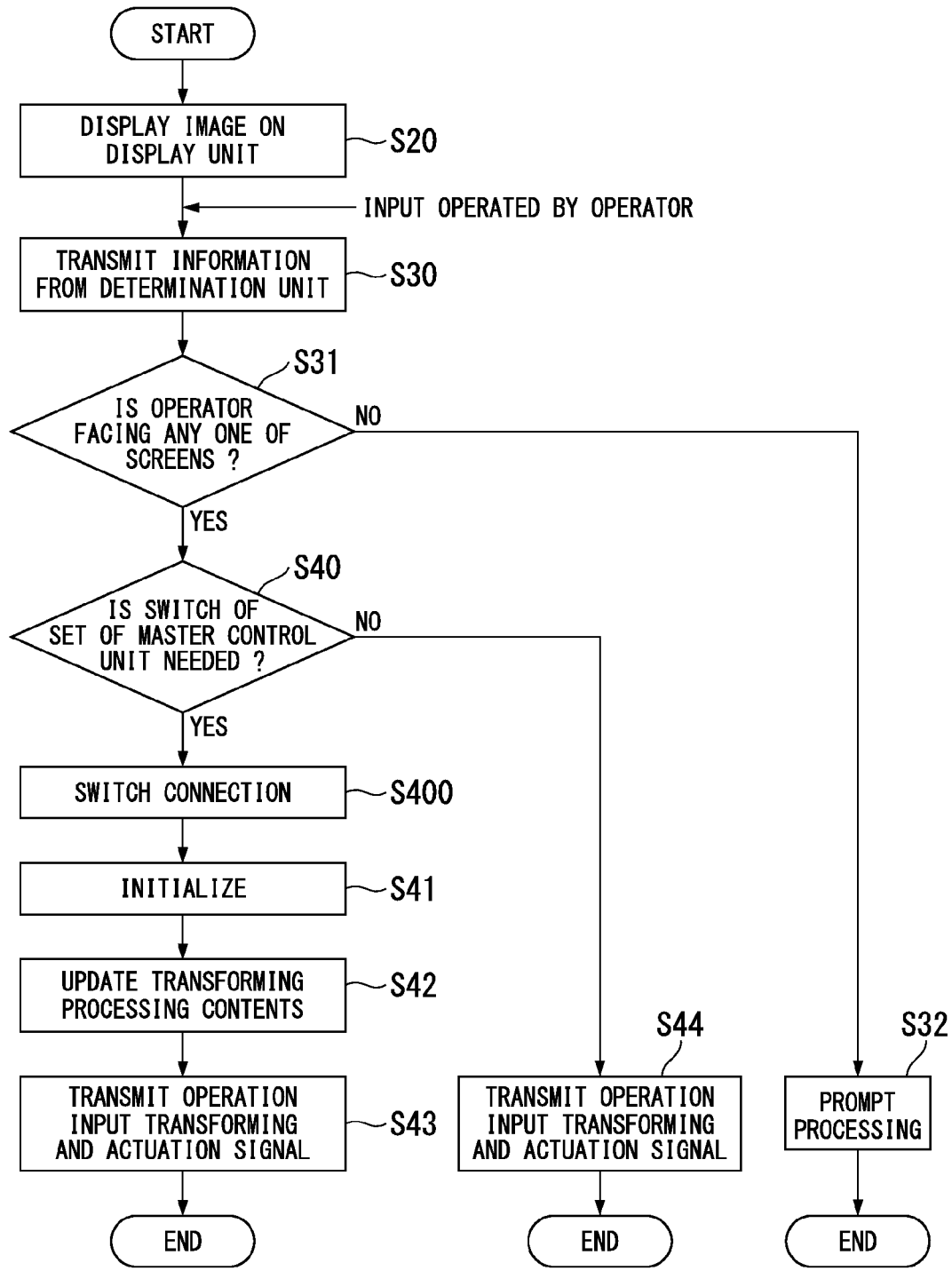
FIG. 9 is a flowchart showing a flow of actuations of the medical master slave manipulator system according to the third embodiment of the present invention.

FIG. 9 is a flowchart showing a flow of actuations of the master slave manipulator 71. In the master slave manipulator 71, a step of setting a rotation angle θ is not performed. When the imaging devices 32A and 32B arrive at areas at which the manipulations are performed in the body of the patient, in step S20, images acquired by the imaging device are displayed on the first screen 25 and the second screen 26.

When the determination result of step S40 is Yes, in step S400, the master control unit 41 transmits a command to the switch unit 72, and switches the connection such that the slave manipulator, which is currently not connected, is connected to the manipulator control unit 42. Thereafter, the initialization of step S41 is performed.

Configurations other than those described above are basically same as the first embodiment.

Even in the master slave manipulator 71 of the present embodiment, as the operator Op is merely facing the screen more appropriate for the manipulation or operation to be performed, the contents of the transforming processing of the master control unit are automatically updated. As a result, the operator can intuitively operate the master arm while looking at the screen, and thus, can operate the slave arm of the switched slave manipulator with no stress.

In addition, the master slave manipulator 71 of the present embodiment includes the plurality of slave manipulators, and thus, manipulations can be appropriately performed with respect to a plurality of patients or diseased parts.

In the present embodiment, three or more slave manipulators may be provided.

As will be apparent from the description of the first embodiment and the third embodiment, in the present invention, "a plurality of different images of an object" is a concept including the case in which the object is one and the case in which the object is plural.

A fourth embodiment of the present invention will be described with reference to FIGS. 10 and 11. The master slave manipulator 81 of the present embodiment is distinguished from the above-mentioned master slave manipulator 1 in that a slave manipulator includes a plurality of imaging devices.

Figure 10:
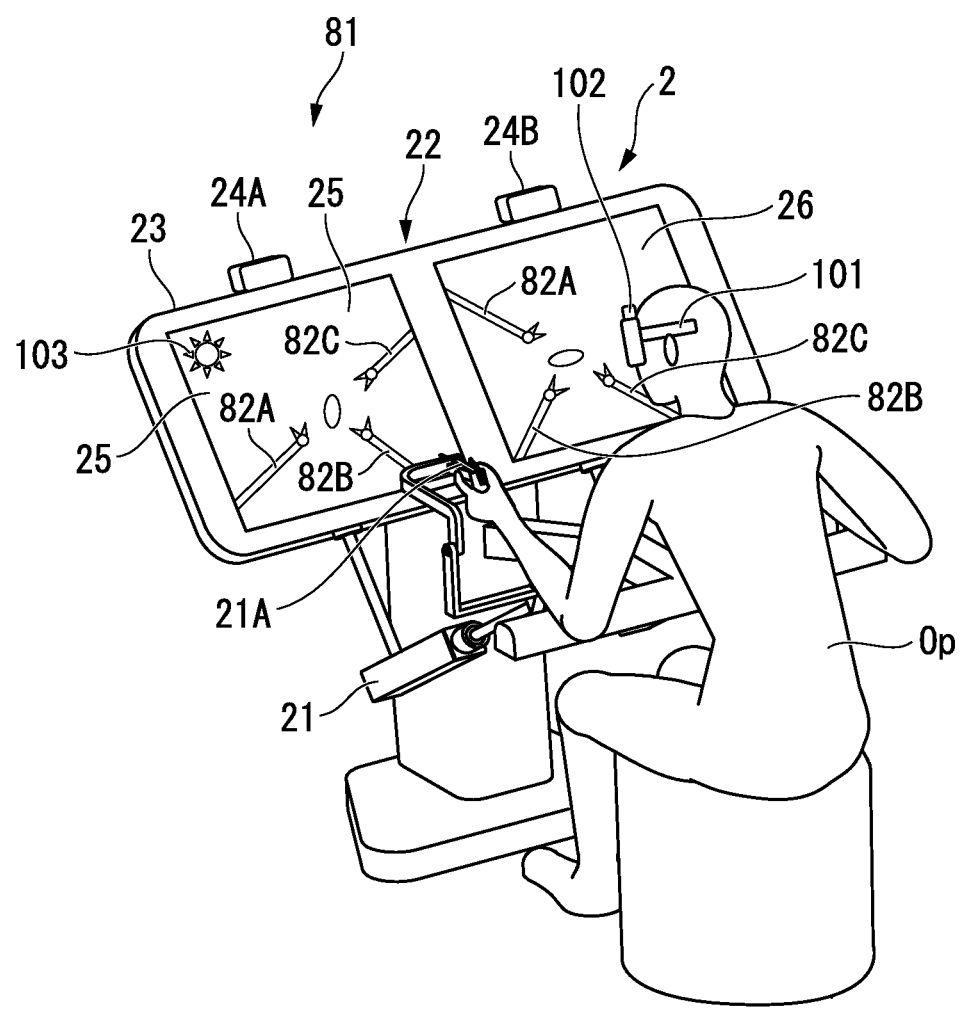
FIG. 10 is a diagram showing a master input device of a medical master slave manipulator system according to a fourth embodiment of the present invention.
Figure 11:
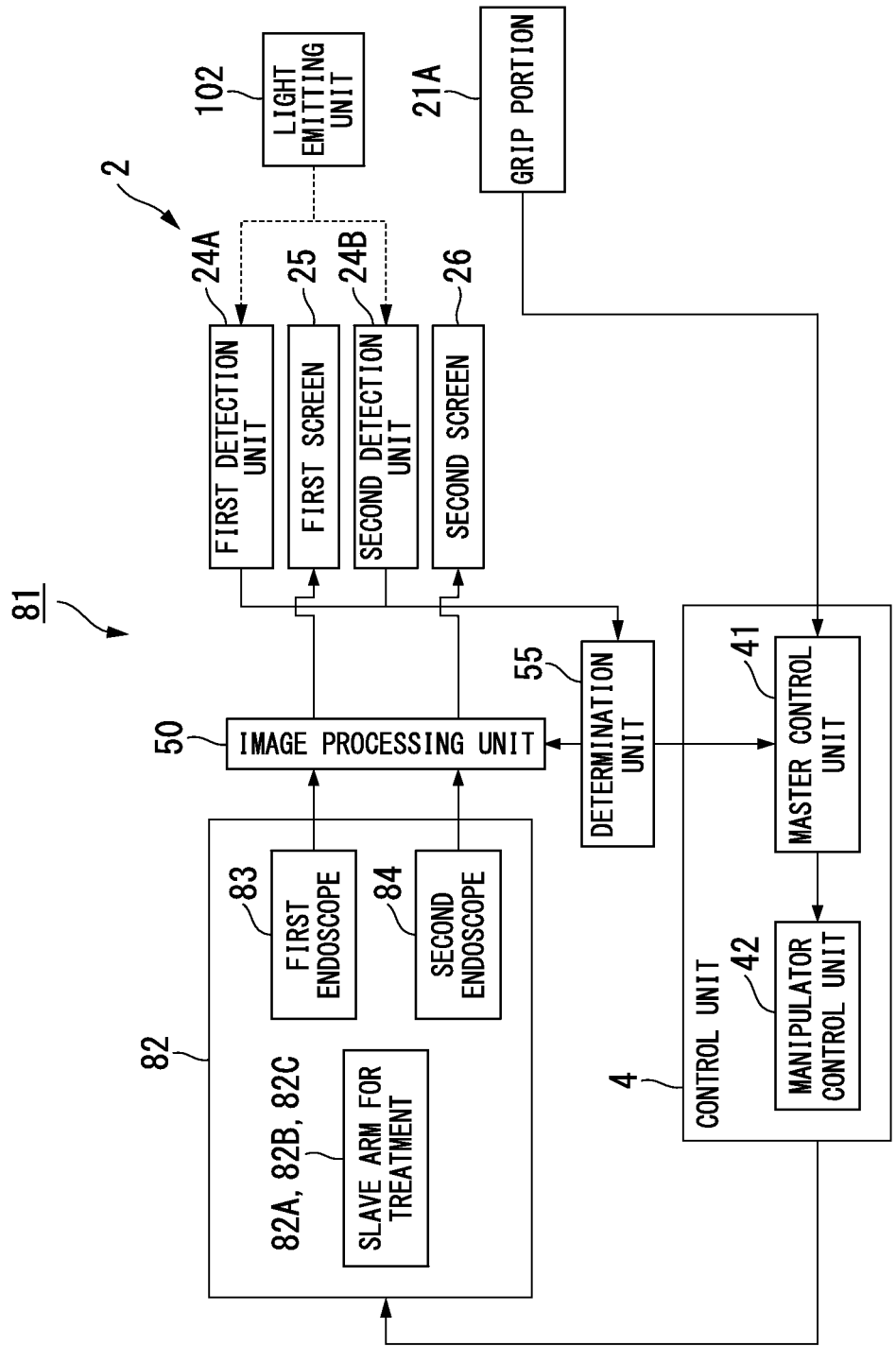
FIG. 11 is a functional block diagram of the medical master slave manipulator system according to the fourth embodiment of the present invention.

FIG. 10 is a diagram showing the master input device 2 of the master slave manipulator 81. FIG. 11 is a functional block diagram of the master slave manipulator 81. A slave manipulator 82 includes three slave arms 82A, 82B and 82C for treatment. The same image as the second embodiment is displayed on the first screen 25 and the second screen 26.

However, the slave manipulator includes two imaging devices, a first endoscope 83 and a second endoscope 84. An image acquired by the first endoscope 83 is displayed on the first screen 25. An image acquired by the second endoscope 84 is displayed on the second screen 26. Accordingly, the image displayed on the second screen 26 is not the image in which the image processing is performed on the image of the first screen.

Figure 12:
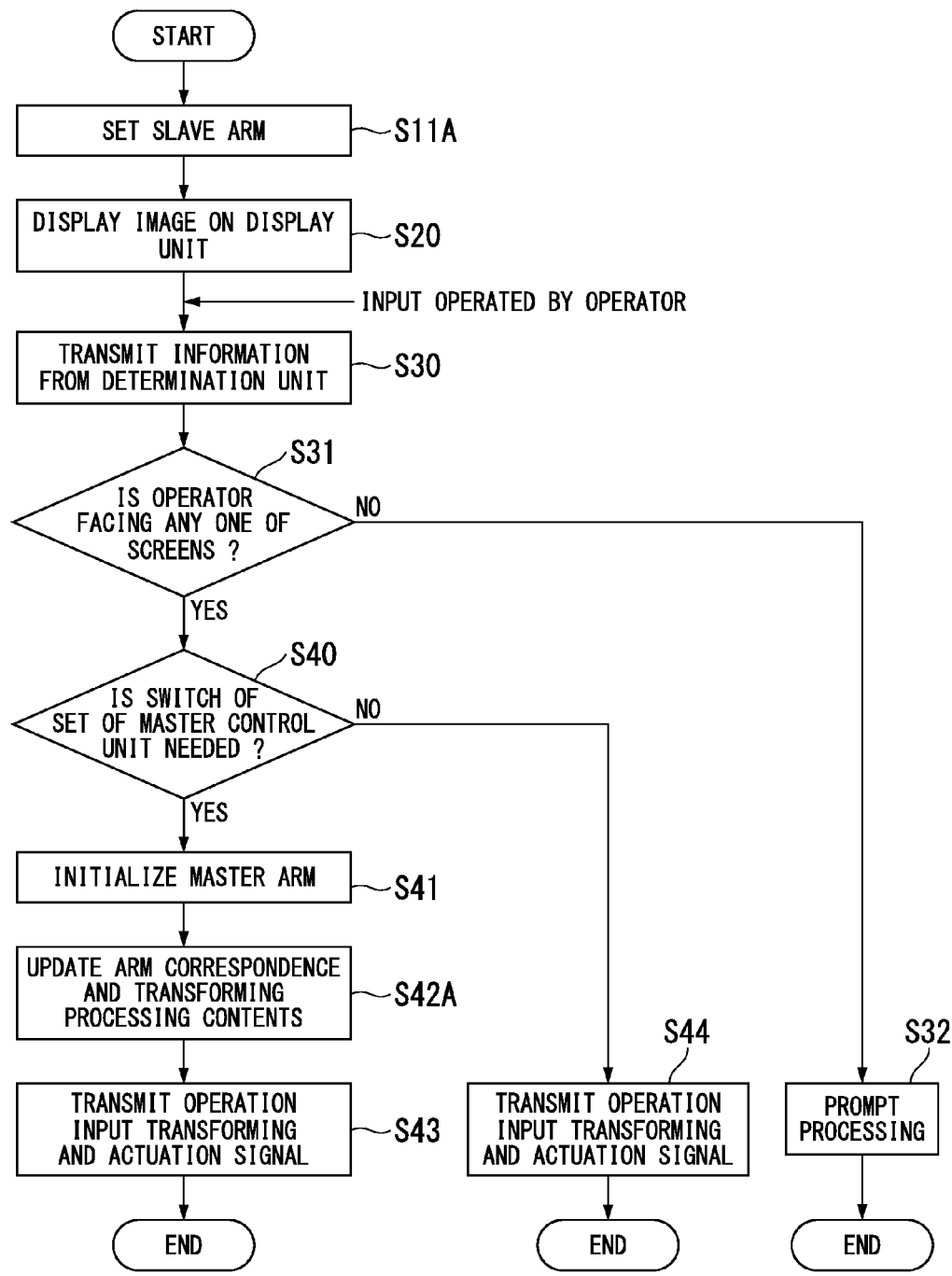
FIG. 12 is a flowchart showing a flow of actuations of the medical master slave manipulator system according to the fourth embodiment of the present invention.

FIG. 12 is a flowchart showing a flow of actuations of a master slave manipulator 81. In the master slave manipulator 81, in step S11A, only two slave arms operated by the master arm are set in the first screen 25 and the second screen 26, without setting a rotation angle θ. The contents of the transforming processing in step S42A are automatically calculated based on the positional relation and the like, between the first endoscope 83 and the second endoscope 84.

Configurations other than those described above are basically same as the second embodiment.

Even in the master slave manipulator 81 of the present embodiment, as the operator Op is merely facing the screen more appropriate for the manipulation or operation to be performed, the transforming processing contents of the master control unit are automatically updated. As a result, the operator can intuitively operate the master arm while looking at the screen and thus operate the slave arm with no stress.

In addition, since the master slave manipulator 81 of the present embodiment includes two imaging devices, the first endoscope 83 and the second endoscope 84, various operative field images other than the rotational operative field image can be displayed on the second screen 26. For example, the image acquired in one direction in which the tissue is manipulated is displayed on the first screen 25, and the image acquired in a direction opposite to the one direction in which the same tissue is manipulated is displayed on the second screen, so that each sequence of the manipulation can be performed at an appropriate angle while switching the screen used in the manipulation.

In the above-mentioned example, the example in which the three slave arms for treatment are installed has been described. However, in the present embodiment, the number of slave arms for treatment may be two or fewer or may be four or more, and presence or absence of correspondence relation switching between the master arm and the slave arm for treatment in step S42A may be set according to the number. In addition, in the above-mentioned example, the example in which the two imaging devices are installed has been described. However, instead of that configuration, a configuration in which one imaging device including a plurality of imaging units is used and an image acquired by each imaging unit is displayed on a display unit may be provided. In addition, the endoscopes of the imaging device may not have the same structure. For example, one endoscope may be a direct vision type endoscope and the other endoscope may be a lateral vision type endoscope.

Figure 14:
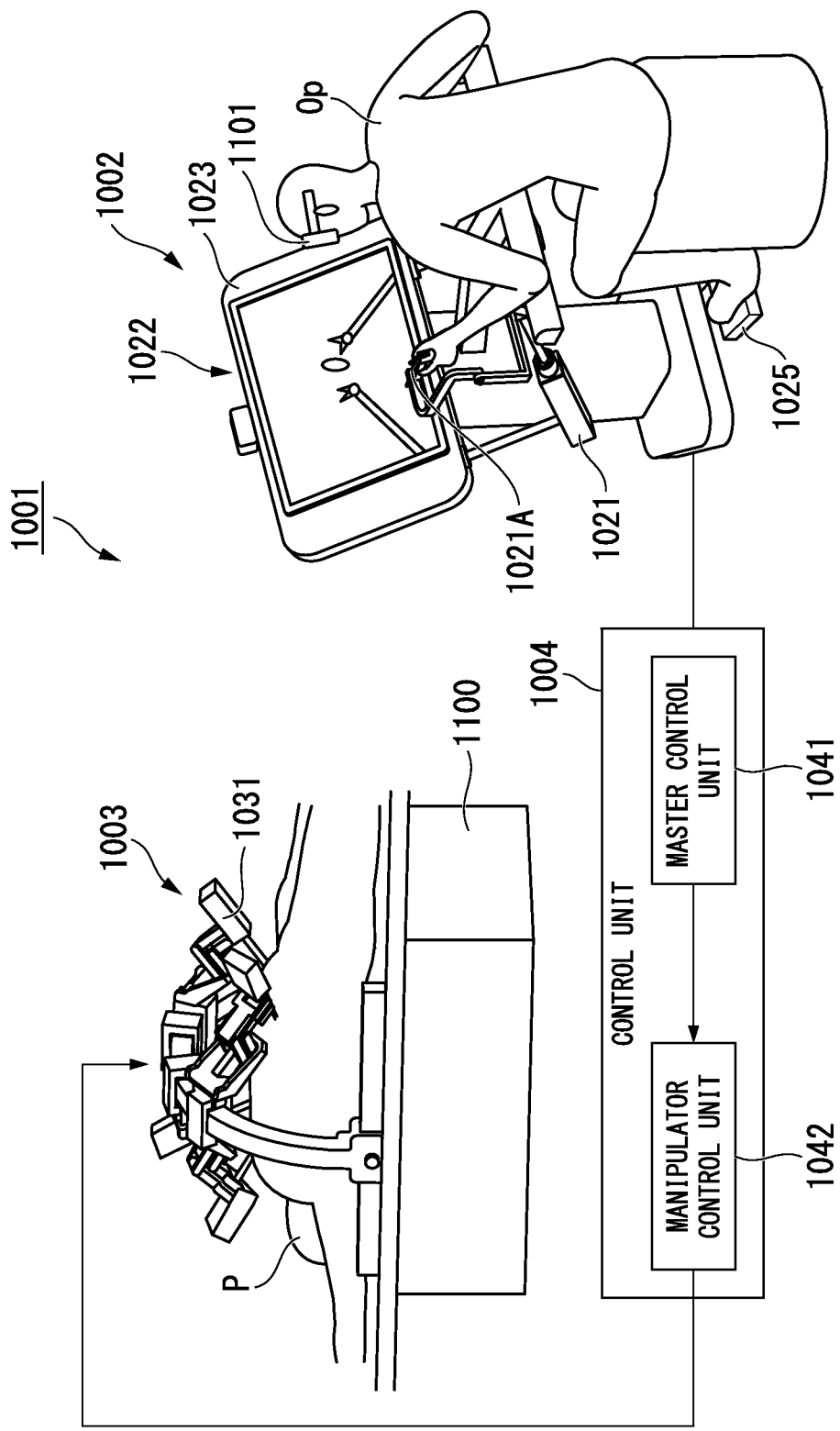
FIG. 14 is a diagram showing a medical manipulator system to which a medical master slave manipulator system according to a fifth embodiment of the present invention is applied.

A fifth embodiment of the present invention will be described. FIG. 14 is a diagram showing a medical manipulator system to which a medical master slave manipulator system (hereinafter, simply referred to as "a master slave manipulator") 1001 of the present embodiment is applied. The master slave manipulator 1001 includes a master input device 1002 having a master arm 1021 and sending an operation command, and a slave manipulator 1003 having a slave arm 1031. The master slave manipulator 1001 is a system for remotely controlling the slave arm 1031 to follow an operation of the master arm 1021 by an operator (surgeon) Op. The operation command via the master arm 1021 is transmitted to a master control unit 1041 of a control unit 1004 and input into a manipulator control unit 1042 after transforming processing (described later) is performed according to the necessity. Thereafter, an actuation signal is transmitted from the manipulator control unit 1042 to the slave manipulator 1003 to actuate the slave arm 1031.

As shown in FIG. 14, the slave manipulator 1003 includes a plurality of slave arms 1031, and is installed at an operating table 1100 on which the patient P is laid. Each of the slave arms has a plurality of joints with multiple degrees of freedom, and is configured to realize a multi-axis actuation. Each of the joints with multiple degrees of freedom is individually driven by a power unit (not shown). As the power unit, for example, a motor (a servo motor) having a servo mechanism provided with an incremental encoder, a speed reducer or the like can be used.

An imaging device (not shown) such as an endoscope for acquiring an image of an operative field including an area to be manipulated (an object) is attached to one of the plurality of slave arms 1031. A treatment instrument (not shown) for performing various treatments is attached to another slave arm. The imaging device or the treatment instrument may be a well-known device appropriately selected and used. In addition, the slave arms include a plurality of power units (not shown) for driving the mounted treatment instruments or the like. A servo motor, for example, can also be employed as the power unit. In addition, in the following description, among the slave arms, the slave arm to which the treatment instrument is attached may be referred to as "a slave arm for treatment."

The master input device 1002 includes a plurality of master arms 1021 operated by the operator Op, and a display unit 1022 on which the image acquired by the above-mentioned imaging device is displayed. Each of the master arms 1021 includes a well-known structure to realize multiaxial actuation. Each of the master arms 1021 includes a grip portion (an operation unit) 1021A disposed at a distal end thereof near the operator Op and gripped by the operator.

Figure 15:
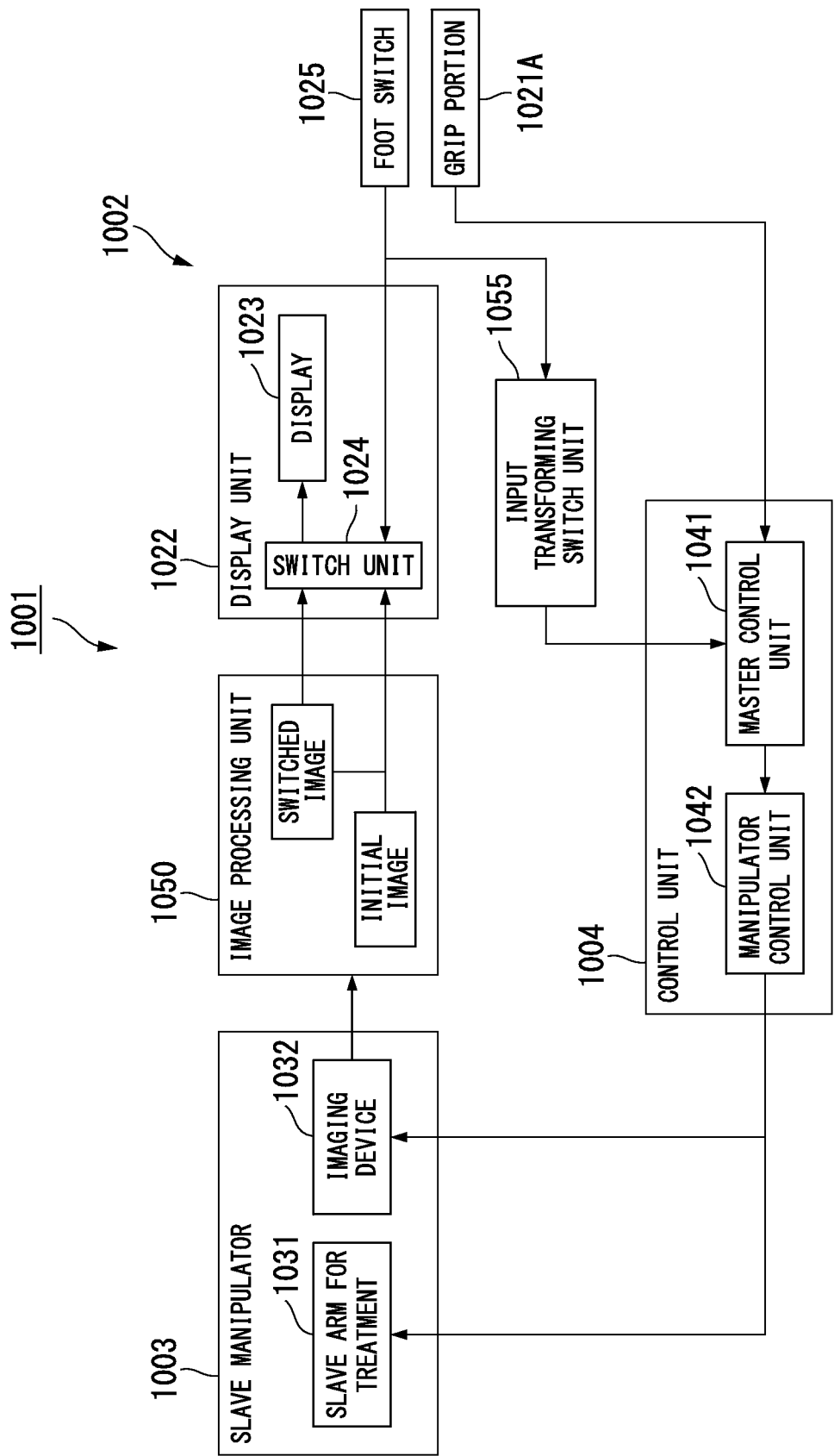
FIG. 15 is a functional block diagram of the medical master slave manipulator system according to the fifth embodiment of the present invention.

FIG. 15 is a functional block diagram of the master slave manipulator 1001. As shown in FIGS. 14 and 15, the display unit 1022 includes a display 1023 on which an image is displayed, and a switch unit (an image selection device) 1024 configured to switch the image displayed on the display 1023.

An image of an operative field acquired by the imaging device is displayed on the display 1023. In the present embodiment, two images having deviation corresponding to a parallax error are projected on the display 1023. The operator Op can three-dimensionally look at the image of the display 1023 through well-known 3D glasses 1101 including a polarization mechanism, a shutter mechanism or the like.

The switch unit 1024 selectively connects the image signal transmitted from an image processing unit (described later) to the display 1023 to display the predetermined image on the display 1023. In the present embodiment, the switch unit 1024 is actuated as the operator Op steps on the foot switch 1025 shown in FIG. 14. However, the input mechanism for actuating the switch unit 1024 is not particularly limited, but various switches can be appropriately selected and used.

An image processing unit 1050 is installed between an imaging device 1032 and a display unit 1022. The image processing unit 1050 is a well-known processing circuit or processing program. The image signal transmitted from the imaging device 1032 is processed in a state in which the image can be displayed in the image processing unit 1050, and then an image signal is generated. The processed image signal is displayed on the display 1023 of the display unit 1022.

An input transforming switch unit 1055 is installed between the foot switch 1025 and the master control unit 1041. The input transforming switch unit 1055 transmits the transforming processing contents to the master control unit 1041 such that the slave arm 1031 displayed on the display 1023 is intuitively operated by the master arm 1021 based on the information transmitted from the foot switch 1025.

An actuation of the master slave manipulator 1001 configured as described above will be described.

Figure 16:
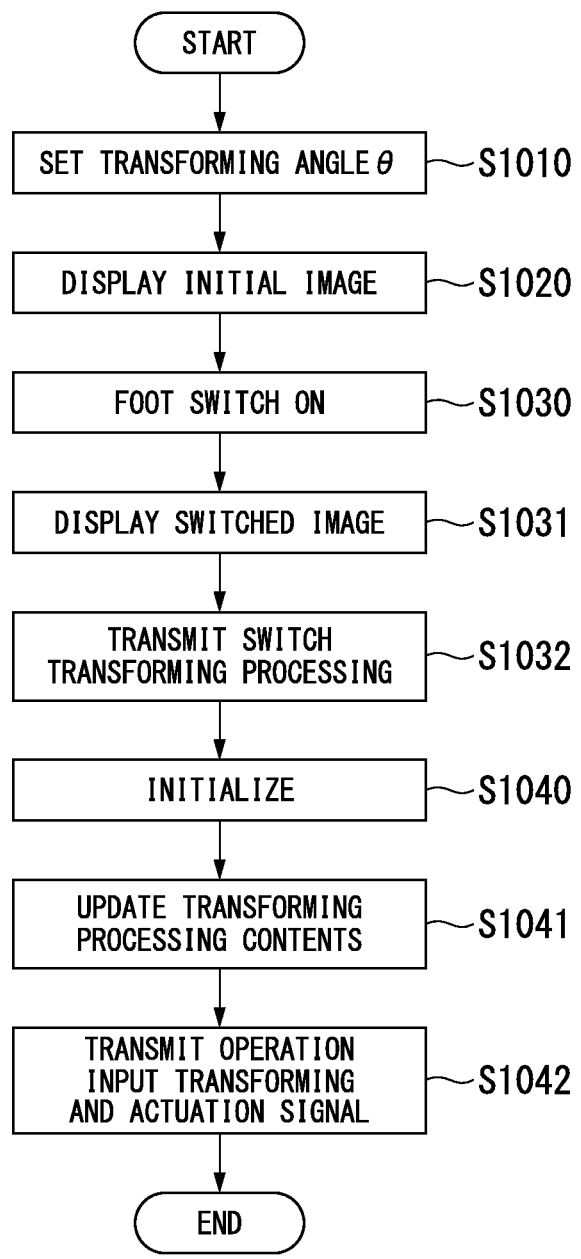
FIG. 16 is a flowchart showing a flow of actuations of the medical master slave manipulator system according to the fifth embodiment of the present invention.

FIG. 16 is a flowchart showing a flow of actuations of the master slave manipulator 1001.

First, in step S1010, the operator Op sets conditions of the image intended to be displayed when the foot switch 1025 is pushed down. Here, as an example, an image (a switched image) in which an image (an initial image) of the operative field acquired by the imaging device is rotated 90 degrees rightward is displayed. In this case, the operator Op inputs the rotation angle θ (90 degrees rightward) into the master input device 1002 via an interface (not shown) to set generation conditions of the switched image.

The input generation conditions of the switched image are transmitted to the image processing unit 1050 and the input transforming switch unit 1055. According to the above, in the input transforming switch unit 1055, based on the generation conditions, the contents of the transforming processing (hereinafter referred to "switch transforming processing") are automatically calculated to match the moving direction of the master arm with the moving direction of the slave arm upon display of the switched image, and temporarily stored in a storage unit such as ROM or RAM.

When the image signal is transmitted from the imaging device 1032, in step S1020, the image processing unit 1050 performs processing for displaying the initial image with respect to the image signal to generate an initial image signal (a first image signal), and displays the signal on the display 1023 as it is. Simultaneously, image processing in response to the generation conditions input with respect to the initial image signal in step S1010 is performed, and a switched image signal (a second image signal) for displaying the switched image is generated. That is, while the image processing unit 1050 normally generates the initial image signal and the switched image signal, at first, only the initial image is displayed on the display 1023 by the setting of the switch unit 1024.

The operator operates the master arm 1021 while looking at the image displayed on the display 1023. The operation command to the master arm 1021 is transmitted to the manipulator control unit 1042, in which a predetermined initial transforming is performed in the master control unit 1041, and transmitted to the slave manipulator 1003 to actuate the slave arm 1031. The master control unit 1041 continues the processing of the operation command by the initial transforming until the foot switch 1025 is pushed down.

When the operator Op performs the manipulation while looking at the switched image, the operator Op pushes down the foot switch 1025 in step S1030. Then, in step S1031, the switch unit 1024 changes the setting such that the switched image signal generated at the image processing unit 1050 is transmitted to the display 1023. Then, the switched image is displayed on the display 1023.

The signal of the foot switch 1025 is also transmitted to the input transforming switch unit 1055. Accordingly, in step S1032, the input transforming switch unit 1055 transmits temporarily stored switch transforming processing to the master control unit 1041.

The master control unit 1041 in which the information is received from the input transforming switch unit 1055 performs, in step S1040, initialization to match a position and an orientation of a grip portion 1021A of the master input device 1002 with a position and an orientation of a distal end of the slave arm 1031 for treatment displayed in the switched image. The master control unit 1041 calculates a difference between the position and orientation of the grip portion 1021A and the position and orientation of the distal end of the slave arm 1031 for treatment in the switched image, and actuates the driving unit of the master input device 1002 such that the difference becomes zero, performing the initialization of the grip portion 1021A. At this time, a message such as "Initialization is in process. Please keep hands away from the grip portion," and so on, may be displayed on the display unit 1022 to prompt the operator.

In addition, the "position" of the master arm and slave arm is a three-dimensional position represented by an XYZ coordinate system of a predetermined area (for example, the grip portion 1021A and the distal end of the treatment instrument, and so on) of the master arm and the slave arm. The "orientation" of the master arm and the slave arm means a direction of the distal end with respect to the predetermined area as a reference point. In addition, in the master slave manipulator, the position and orientation matching is a conventional technique, and a specific method thereof is not limited to the above.

Next, in step S1041, the contents of the transforming processing of the operation command in the master control unit 1041 are updated to the switch transforming processing received from the input transforming switch unit 1055. Accordingly, the master control unit 1041 transforms the operation command such that an actuation direction of the grip portion 1021A coincides with an actuation direction of the distal end of the slave arm 1031 for treatment in the switched image selected by the operator Op. After the transforming processing contents are updated, in step S1042, the master control unit 1041 transforms the operation command related to the screen selected by the operator Op, and transmits the actuation signal to the manipulator control unit 1042. Then, the processing is terminated.

In addition, when the operator Op pushes down the foot switch 1025 once more, the image of the display 1023 is switched to the initial image. Then, after the initialization of the master arm 1021, the transforming processing of the master control unit 1041 is updated to the initial transforming.

According to the master slave manipulator 1001 of the present embodiment, when the operator Op pushes down the foot switch 1025, the image of the display 1023 is switched by the switch unit 1024 to the switched image of the condition previously set by the operator Op. Further, the contents of the transforming processing of the master control unit 1041 are updated to perform the switch transforming processing related to the switched image such that a moving direction of the distal end of the slave arm 1031 for treatment in the switched image is equal to a moving direction of the grip portion 1021A. Accordingly, as the operator merely switches the image displayed on the display 1023 using the foot switch 1025, the contents of the transforming processing of the master control unit can be automatically adjusted, and the operator can intuitively operate the grip portion while looking at the desired image, and thus intuitively operating the slave manipulator with no stress.

In addition, upon switching of the image, the initialization of the position and orientation of the grip portion 1021A is performed. For this reason, in addition to the actuation direction of the grip portion 1021A, a relation of the position and orientation of the grip portion 1021A is also automatically matched with the distal end of the slave arm 1031 for treatment. Accordingly, the operator can intuitively perform the operation.

Further, the switched image is generated by performing the image processing on the image acquired by the imaging device 1032. For this reason, it is not necessary for the operator Op to drive the imaging device 1032 to perform the manipulation at different viewpoints. Accordingly, a time lag generated according to the switching of the view point is removed, and the operator can smoothly perform a series of manipulations. In addition, since interference with another slave arm can be prevented by the driving of the imaging device, reliability of the manipulation is improved.

In the present embodiment, while an example in which the master control unit 1041 drives the master input device 1002 to perform the initialization has been described, the operator may perform the initialization with manual operations. For example, without installing the driving unit at the master input device 1002, a switch for switching On/Off of transmission of the operation command from the master input device to the master control unit is installed. Then, a configuration in which the operator moves the grip portion 1021A to a desired position intended as the initial position while pushing the switch and pushes down the foot switch 1025 once more to complete the initialization may be provided. In this case, the position and orientation of the grip portion may not completely match the position and orientation of the distal end of the slave arm. However, since the slave arm is operated based on a difference value of a movement from the initial position with a priority of the initial position set by the operator, the operator can intuitively perform the operation at the setting in which the operator can most easily operate.

In addition, the image processing, which becomes the generation conditions of the switched image, is not limited to the above-mentioned rotation processing but may be scaling processing or the like. In this case, when the manipulation is performed while looking at the initial image and when the manipulation is performed while looking at the switched image, as a motion scale ratio between the master arm and the slave arm is varied, the intuitive operation can be continuously performed. For this reason, information of the motion scale ratio may be included in the switch transforming processing. Here, a plurality of image processings may be combined to set the generation conditions of the switched image.

Further, two or more kinds of switched images may be set. In this case, for example, the initial image and each switched image may be sequentially switched by pushing the foot switch 1025.

Furthermore, instead of normal generation of the switched image, the switched image may be generated and displayed on the display 1023 when the foot switch 1025 is pushed down.

In addition, the switched image in which the rotation processing is performed according to the image processing maintains the 3D display so that the operator can visually confirm the image after the switching. For example, in the 3D display, while two images corresponding to binocular disparity are displayed on the same screen, in consideration of the binocular disparity corresponding to the rotation amount upon the image processing, the two images are re-transformed to maintain the 3D display, and are displayed on a display device.

A sixth embodiment of the present invention will be described with reference to FIGS. 17A, 17B and 18. The master slave manipulator 1061 of the present embodiment is distinguished from the above-mentioned master slave manipulator 1001 in that correspondence relation between the master arm and the slave arm is switched when the image of the display unit is switched. In addition, in the following description, same elements in the above description are designated by same reference numerals, and a description thereof will not be repeated here.

Figure 17A:
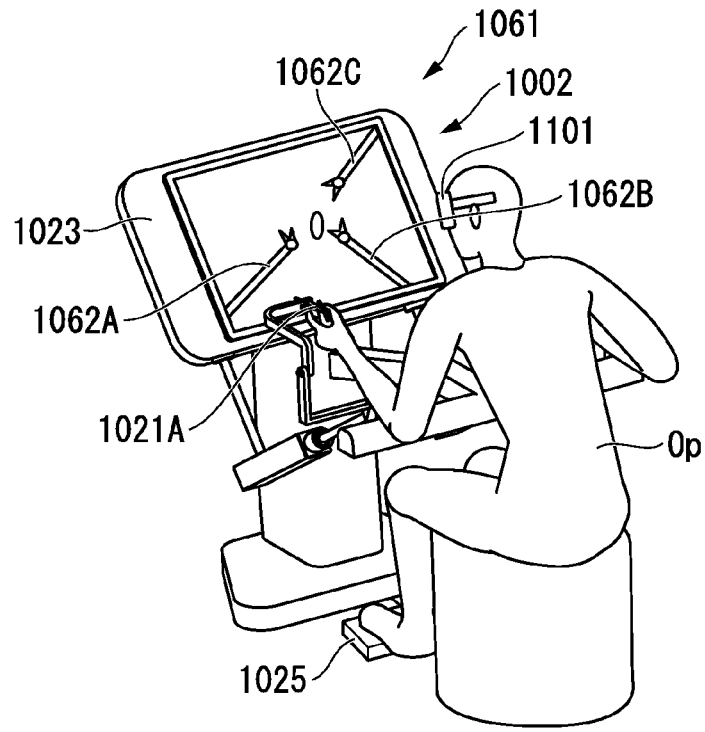
FIG. 17A is a diagram showing a master input device in a medical master slave manipulator system according to a sixth embodiment of the present invention.
Figure 17B:
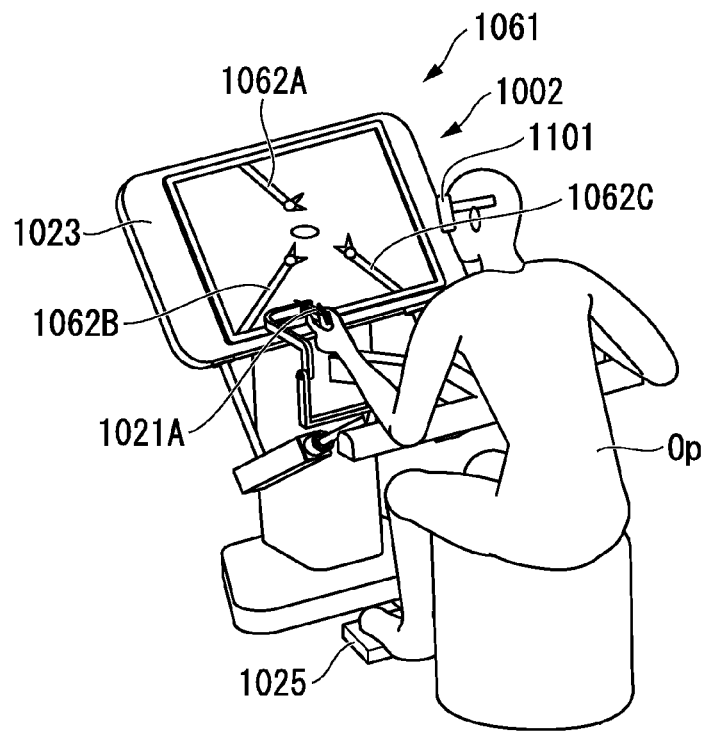
FIG. 17B is a diagram showing the master input device in the medical master slave manipulator system according to the sixth embodiment of the present invention.

Both of FIGS. 17A and 17B are diagrams showing the master input device 1002 of the master slave manipulator 1061. As shown in the display 1023, three slave arms 1062A, 1062B and 1062C for treatment are installed at the slave manipulator 1003. When the initial image is displayed on the display 1023, as shown in FIG. 17A, the slave arms 1062A and 1062B are disposed at a position at which the intuitive operation is easily performed by the operator Op. When the switched image in which the initial image is rotated 90 degrees rightward is displayed on the display 1023, as shown in FIG. 17B, the slave arms 1062B and 1062C are disposed at a position at which the intuitive operation is easily performed by the operator Op.

Only two master arms are installed at the master input device 1002. For this reason, in the present embodiment, the two slave arms for treatment and the two master arms, which are easily and intuitively operated, are related to each other in the initial image and the switched image, respectively. That is, according to the image displayed on the display 1023 of the display unit 1022, correspondence relation between the master arms and the slave arms for treatment is varied.

Figure 18:
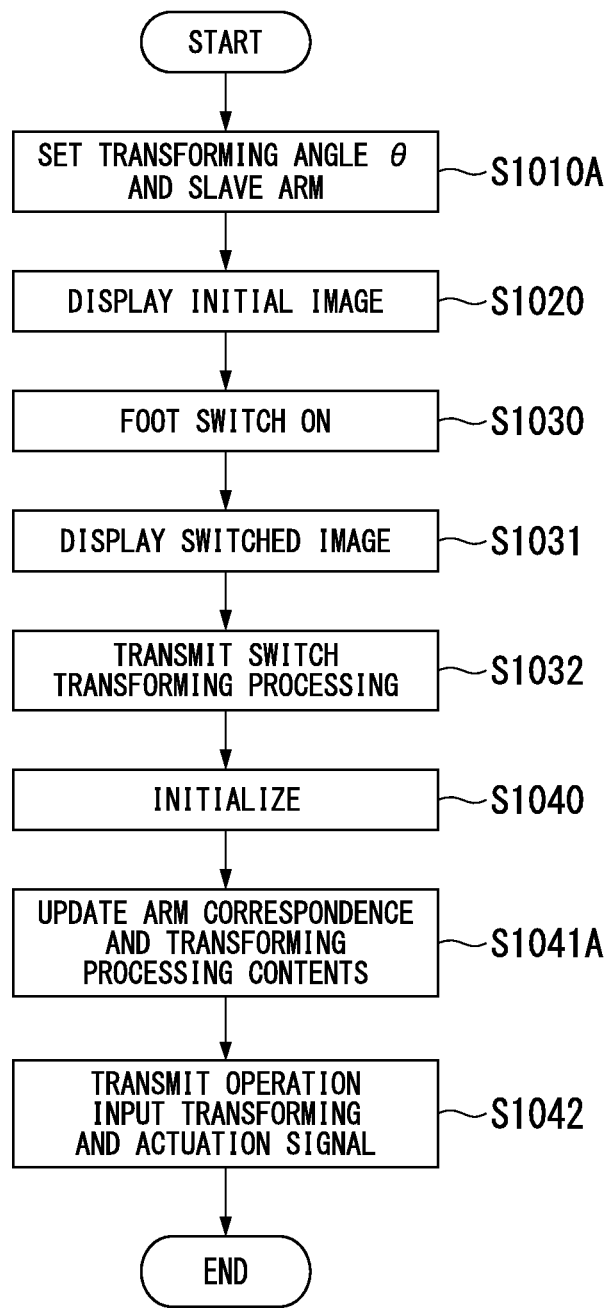
FIG. 18 is a flowchart showing a flow of actuations of the medical master slave manipulator system according to the sixth embodiment of the present invention.

FIG. 18 is a flowchart showing a flow of actuations of the master slave manipulator 1061. In step S1010A, similar to the sixth embodiment, a transforming angle θ which is the generation conditions of the switched image is set. In addition, two slave arms for treatment operated by the master arm 1021 are set by the operator Op in the initial image and the switched image, respectively.

Thereafter, in step S1040, the initialization is performed such that the positions and orientations between the distal ends of the two slave arms and the grip portions set in step S1010A are matched. Next, in step S1041A, correspondence relation between the master arm and the slave arm and the contents of the transforming processing of the operation command are updated.

Configurations other than those described above are basically same as the sixth embodiment.

Even in the master slave manipulator 1061 of the present embodiment, as the image displayed on the display 1023 is merely switched, the contents of the transforming processing of the master control unit are automatically updated. For this reason, as the operator intuitively operates the master arm while looking at the selected image, the slave arm can be intuitively operated with no stress.

Further, since the correspondence relation between the master arm and the slave arm is also automatically updated, in each screen, the slave arm can be optimally operated to perform the manipulation.

In the present embodiment, an example in which three slave arms for treatment are installed has been described. However, two slave arms for treatment may be installed. In addition, four or more slave arms for treatment may be installed. Further, instead of the setting the slave arm, which is operated, while looking at the generation conditions of the switch image and each image in step S1010A, the master control unit or the like may automatically calculate a rotation angle at which the two slave arms differently combined than the first screen are easily operated, based on the positional relation between the imaging device and each of the slave arms for treatment, and determine a transforming angle θ. Here, the positional relation between the imaging device and each of the slave arms for treatment may be calculated from the initial image and the switched image acquired by the imaging device, and may be calculated from the position information based on a value or the like of the encoder of the slave arm.

In addition, the optimal correspondence between the slave arm and the master arm may be automatically calculated from the transforming angle θ determined in step S1010A based on the positional relation information between the imaging device and the slave arm. Even in this case, similar to the above, the positional relation between the imaging device and each of the slave arms may be calculated from the image acquired by the imaging device, and may be calculated from the position information based on a value or the like of the encoder of the slave arm.

As another method, the correspondence between the slave arm and the master arm may be selected again by the operator after the switched image is displayed in step S1031. An alternative method may be performed by an input switch such as an interface or the like.

A seventh embodiment of the present invention will be described with reference to FIGS. 19 and 20. The master slave manipulator 1071 of the present embodiment is distinguished from the above-mentioned master slave manipulator 1001 in that the switched image is generated based on an initial image before the driving when the imaging device is driven.

Figure 19:
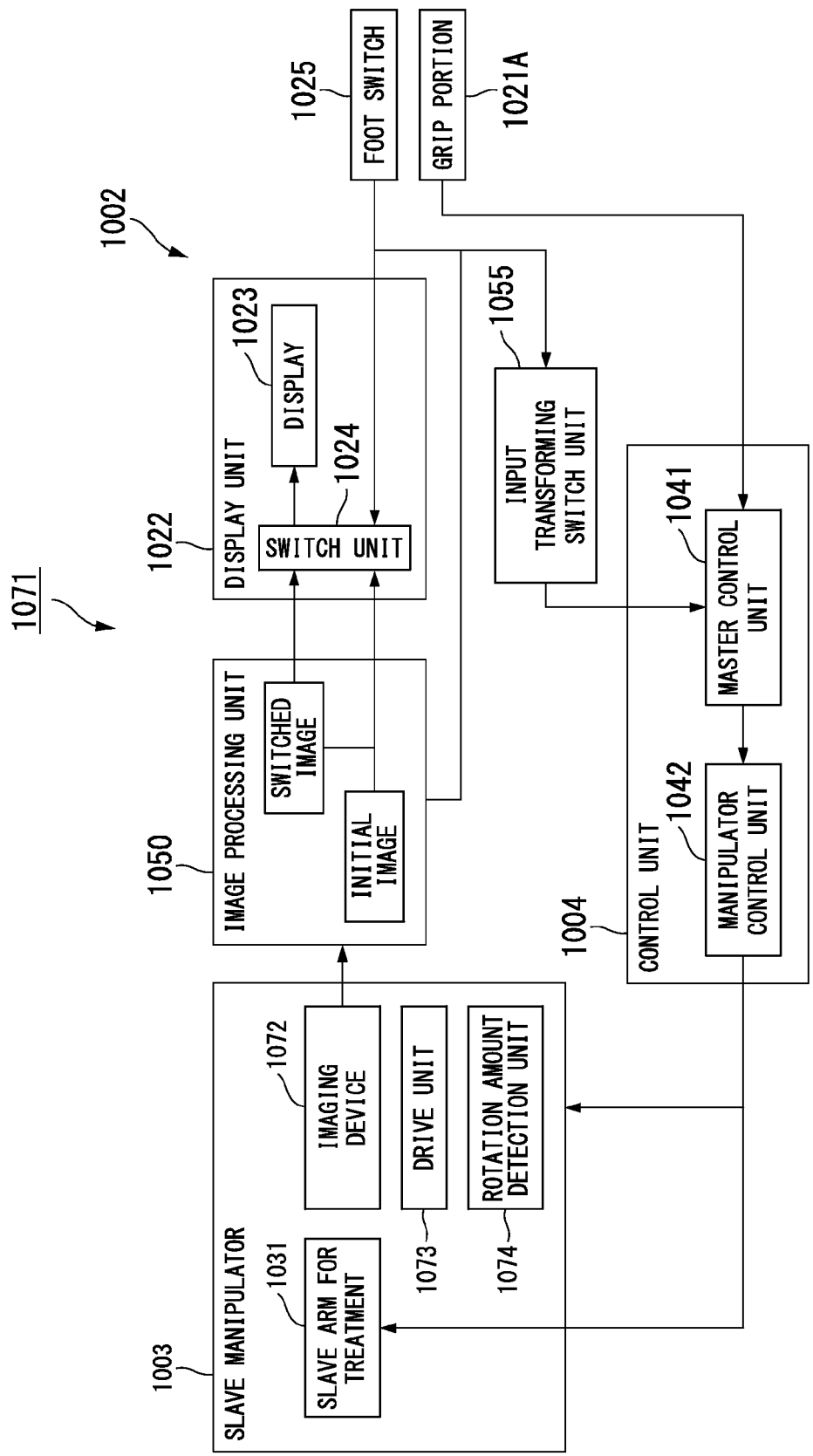
FIG. 19 is a functional block diagram of a medical master slave manipulator system according to a seventh embodiment of the present invention.

FIG. 19 is a functional block diagram of the master slave manipulator 1071. The overall configuration of the master slave manipulator 1071 is basically similar to that of the master slave manipulator 1001 of the fifth embodiment. An imaging device 1072 of the master slave manipulator 1071 includes a driving unit 1073. Then, as the driving unit 1073 is driven, a field of vision of the acquired image can be rotated. In addition, the imaging device 1072 also includes a rotation amount detection unit 1074 constituted by a rotary encoder, and so on. Then, a rotation angle of the imaging device 1072 according to the driving of the driving unit 1073 can be detected.

In the present embodiment, the signal of the foot switch 1025 is also transmitted to the image processing unit 1050, in addition to the switch unit 1024 and the input transforming switch unit 1055.

An actuation of the master slave manipulator 1071 configured as described above will be described.

The operation not according to the driving of the imaging device 1072 is basically similar to the fifth embodiment. When the manipulation using the image of the rotation angle different from any one of the initial image and the switched image set in step S1010 is intended to be performed, the operator Op drives the driving unit 1073 by the operation command from the master arm 1021 or the like, rotates the imaging device 1072, and searches for the image that becomes an appropriate operative field, updating the initial image.

Figure 20:
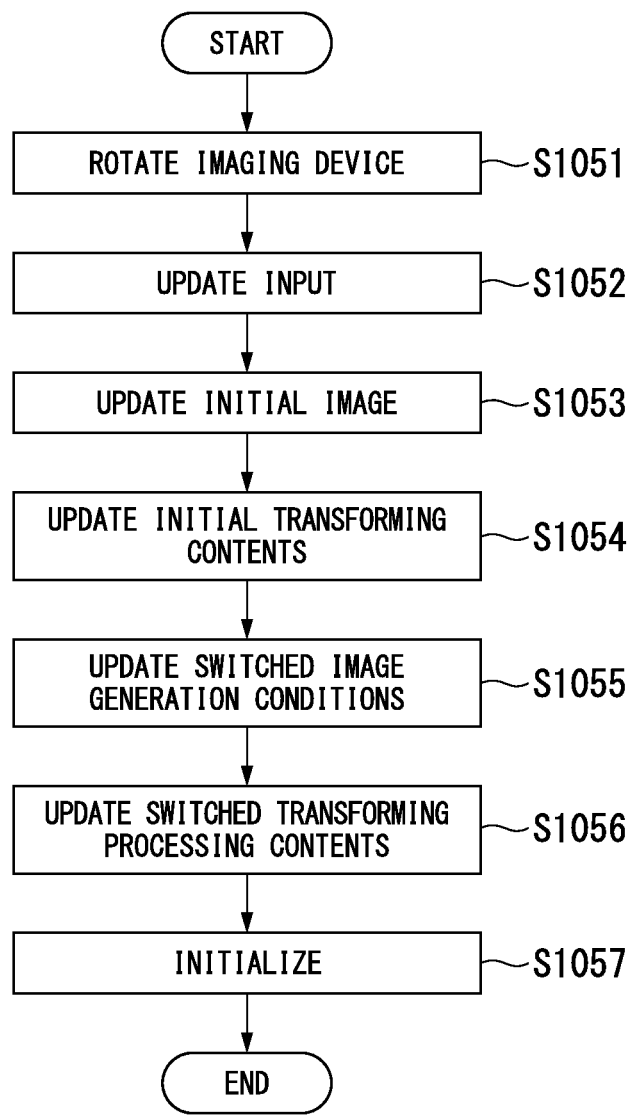
FIG. 20 is a flowchart showing a flow of actuations when an initial image is updated in the medical master slave manipulator system according to the seventh embodiment of the present invention.

FIG. 20 is a flowchart showing a flow of updating the initial image. First, in step S1051, the imaging device 1072 is rotated, and search for an appropriate image as an operative field is performed.

In a step in which the image of the imaging device 1072 arrives at a desired state appropriate for the manipulation, in step S1052, the operator Op performs a predetermined update input in which the foot switch 1025 is combined with the operation of another input portion.

In step S1053, the image processing unit 1050, in which the updated input is received, updates the setting thereof such that the image acquired by the imaging device 1072 becomes the initial image upon reception of the updated input.

Next, in step S1054, the input transforming switch unit 1055 calculates the contents of the input transforming processing corresponding to the initial image after the update to transmit the contents to the master control unit 1041. The master control unit 1041 updates the contents of the initial transforming such that the contents of the received input transforming processing become the initial transforming.

Further, next, in step S1055, the image processing unit 1050 updates the generation conditions such that a difference of a rotation angle of the initial image before and after the update becomes the generation conditions of the switched image, based on the information of the rotation amount detection unit 1074. After that, the image processing is performed with respect to the signal of the initial image after the update, and a signal that can display substantially the same image as the initial image before the update is generated as a signal of the switched image.

In step S1056, the input transforming switch unit 1055 calculates the transforming processing corresponding to the switched image after the update, and temporarily stores the transforming processing as the switch transforming processing to the storage unit. In the example, since the initial image before the update becomes the switched image after the update, the contents of the initial transforming are temporarily stored as the switch transforming processing. Thereafter, in step S1057, the initialization of the master arm 1021 is performed to correspond to the initial image after the update. Then, a series of processings are terminated.

In addition, a sequence of the processings from steps S1053 to S1056 is not particularly limited but may be appropriately varied. Further, these steps may be performed after step S1057.

Configurations other than those described above are basically same as the fifth embodiment. That is, when the operator Op pushes down the foot switch 1025, the switched image having the same angle as the initial image before the update, which is generated by performing the image processing on the initial image after the update, is displayed on the display. Then, the switch transforming processing corresponding to the switched image is transmitted to the master control unit 1041 to be applied thereto.

In addition, after the imaging device 1072 is driven, when the foot switch 1025 is pushed down without performing the predetermined operation, the imaging device 1072 is stopped, and the setting of the initial image is updated such that the image having the same angle as the initial image which is generated by performing the image processing on the image acquired by the imaging device 1072 becomes the initial image.

In the master slave manipulator 1071 of the present embodiment, as the driving unit 1073 is driven and the predetermined operation is performed on acquiring the desired image, the initial image most frequently used in the manipulation can be appropriately updated to the desired image.

In addition, the image processing unit 1050 and the input transforming switch unit 1055 are automatically set such that the initial image before the update becomes the switched image. For this reason, as only the foot switch 1025 is operated, the switched image easily returns to substantially the same image as the initial image before the update.

In the present embodiment, instead of the rotation driving of the imaging device, a predetermined operation may be performed after an scaling operation in which an imaging optical system is driven. For example, if the predetermined operation is performed when the image becomes n times the initial image, the n-times image is updated to the initial image and the image processing is performed on the updated initial image so that the image reduced to 1/n times becomes the switched image. In this way, a plurality of appropriate magnifications are set while driving the imaging optical system, and the image with the plurality of magnifications can be appropriately switched, and manipulation is performed.

In addition, in the present embodiment, while an example in which the switched image is one has been described, a configuration in which the above-mentioned predetermined operation is performed plural times and a plurality of switched images can be set may be provided. According to this configuration, the manipulation can be performed on the image in a previous state more than the state before the latest driving, and the manipulation can be more appropriately performed as a plurality of images are used.

While the respective embodiments of the present invention have been described as described above, the scope of the present invention is not limited to the embodiments, but various modifications may be made to various components, the components may be removed, and the configurations of the embodiments may be combined with each other, without departing from the spirit of the invention.

Figure 13:
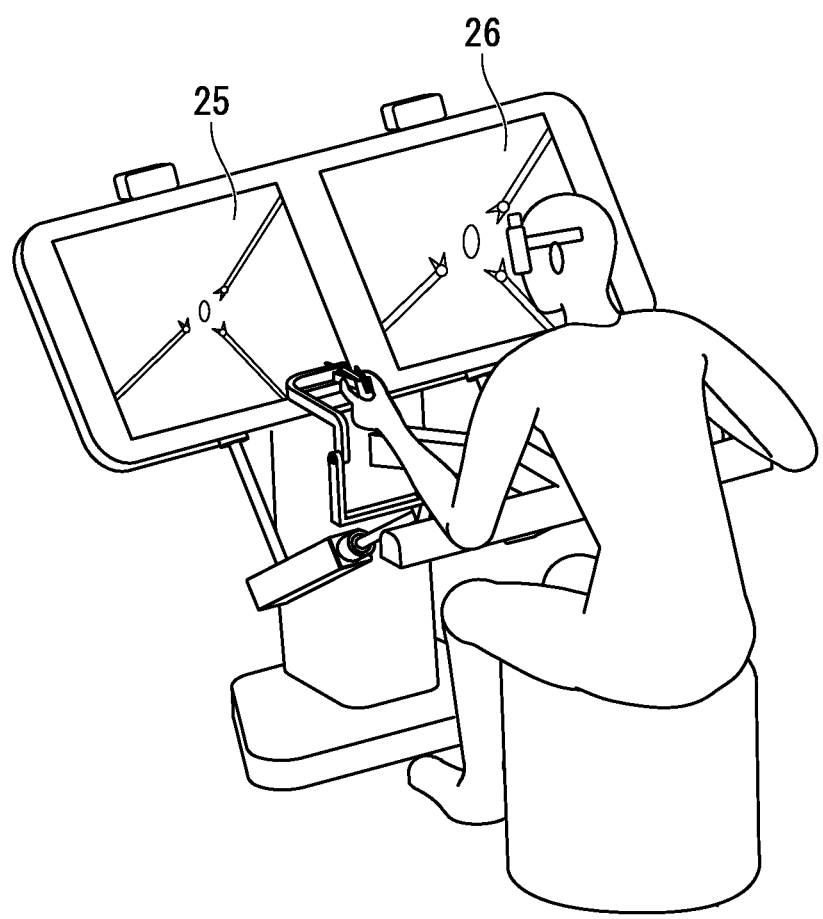
FIG. 13 is a diagram showing a master input device in a medical master slave manipulator system of a variant according to the first to fourth embodiments of the present invention.

In the above-mentioned first to fourth embodiments, for example, when the image displayed on the second screen is generated by the image processing of the image of the first screen, the image processing is not limited to the above-mentioned rotation processing. As an example, as described in the modified example shown in FIG. 13, the image in which the enlargement processing is performed on the image of the first screen 25 may be displayed on the second screen 26. In this case, when the manipulation is performed while looking at the first screen 25 and when the manipulation is performed while looking at the second screen 26, the intuitive operation can be performed as the motion scale ratio between the master arm and the slave arm is varied. For this reason, when the contents of the transforming processing are updated, the motion scale ratio may be varied. Accordingly, when the manipulation is performed while looking at any one of the screens, a relation between the movement amount of the master arm and the movement of the slave arm may not be varied. In addition, the reduction processing may be performed, rather than the enlargement processing.

Further, in the above-mentioned first to fourth embodiments, the example in which the grip portion is connected to the master arm as the operation unit has been described. However, the operation unit may not include the master arm. For example, a position and an orientation of the operation unit or the operator's hands may be acquired by a motion sensor such as a camera or a position sensor.

Furthermore, in the above-mentioned first to fourth embodiments, an example in which the detection unit detects which one of the screens the face of the operator faces, and the contents of the initialization or the transforming processing are updated based on the screen has been described. However, the detection unit may be configured to detect whether the face of the operator is facing any one of the screens based on the position or orientation of the operator. In addition, the screen on which the image selected by the operator to perform the manipulation is displayed may be input by an input portion such as a switch or the like. In the master slave manipulator according to the above-mentioned first to fourth embodiments of the present embodiment, the transforming processing contents are automatically updated based on the image selected by the operator, and the image is intentionally or unintentionally selected in the former case and intentionally selected in the latter case.

The input portion is not limited to the foot switch but may be installed at any place.

In addition, in the above-mentioned first to fourth embodiments, the configuration of the display unit can be variously modified. For example, a screen of a display having one screen may be divided into two display regions, which function as a first screen and a second screen. Further, a head mount display may be used.

Furthermore, two or more screens may be installed to display different operative field images on the respective screens.

In addition, in the above-mentioned fifth to seventh embodiments, the configuration of the display of the display unit may be variously modified. For example, the head mount display may be used. Further, the display having two or more screens or display regions may be used. In particular, in the latter case, when a plurality of switched images are set, some of the plurality of switched images can be previously displayed on the display as the next candidate (and an nth candidate). For this reason, the switching of the image can be more smoothly performed. When the two or more screens or display regions are adjacent to each other, even in the manipulation using the initial image, the switched image of the next candidate can be substantially confirmed with the eye at the peripheral field of vision, and thus, it is more preferable.

In addition, in the above-mentioned fifth to seventh embodiments, as the plurality of switched images are set, an environment for pseudo driving of the imaging device can be made to. For example, when eleven sheets of switched images are set at a rotation angle of 30 degrees and the images are configured to be sequentially displayed by an input mechanism such as a rotation knob or the like, it is possible to perform the image adjustment as if the imaging device is rotated in real time. Since the switched image is generated by the image processing, even when the switched image is enlarged within a certain range, the entire load applied to the master slave manipulator is hardly increased. Further, in the above-mentioned fifth to seventh embodiments of the present embodiment, even when the imaging device cannot be rotated 360 degrees due to restriction of the mechanism, the angle of the image can be adjusted regardless of the restriction.

What is claimed is:

1. A medical master slave manipulator system comprising:
    a master input device configured to send an operation command;
    a slave manipulator operated by the master input device;
    a control unit configured to transmit an operation signal to the slave manipulator based on the operation command;
    a display unit which has a first screen that displays a first image of an object and a second screen that displays a second image of the object, the second image being different from the first image; and
    an image selection device configured so that an operator selects one of the first image and the second image, wherein
    the control unit generates the operation signal that operates the slave manipulator by performing a conversion processing associated with the first image or the second image selected by the operator via the image selection device.

2. The medical master slave manipulator system according to claim 1, wherein the image selection device comprises a detection unit configured to detect any one of the first image and the second image that a face of the operator is facing; and
    the conversion processing associated with the first image or the second image detected by detection unit is performed.

3. The medical master slave manipulator system according to claim 1, wherein the image selection device comprises an input portion configured to select the first image or the second image selected by the operator.

4. The medical master slave manipulator system according to claim 1, wherein at least one of the first image and the second image is generated through image processing of another image.

5. The medical master slave manipulator system according to claim 4, wherein at least one of the first image and the second image is generated through rotation processing of another image.

6. The master slave manipulator system according to claim 4, wherein at least one of the first image and the second image is generated through scaling processing of another image.

7. The medical master slave manipulator system according to claim 1, wherein the first image and the second image are obtained by a plurality of different imaging devices, respectively.

8. The medical master slave manipulator system according to claim 1, wherein the master input device comprises an input device,
    the slave manipulator includes a slave arm,
    the number of slave arms is greater than the number of input devices, and
    in at least one of the conversion processing associated with the image, correspondence between the input device and the slave arm is different from another conversion processing.

9. The medical master slave manipulator system according to claim 8, the medical master slave manipulator system comprises a plurality of the slave manipulators.

10. The medical master slave manipulator system according to claim 1, further comprising an image processing unit configured to generate a first image signal according to the image of the object and a second image signal in which image processing is performed on the first image signal,
    wherein one of the first image signal and the second image signal is displayed on the display unit,
    the image selection device comprises a switch unit configured to switch the image signal displayed on the display unit, and
    when the switch unit switches the image signal displayed on the display unit, the control unit transforms the operation command associated with the image signal displayed on the display unit.

11. The medical master slave manipulator system according to claim 10, wherein the master input device comprises an input device,
    the slave manipulator include a slave arm,
    the number of slave arms is greater than the number of input devices, and
    correspondence between the input device and the slave arm is different from another transforming processing in transforming processing associated with the first image signal and transforming processing associated with the second image signal.

12. The medical master slave manipulator system according to claim 10, further comprising an imaging device including a driving unit and configured to acquire the first image signal,
    wherein, as a predetermined update input is performed after driving the driving unit, contents of transforming processing associated with the first image signal and the first image signal are updated.

13. The medical master slave manipulator system according to claim 12, wherein, when the first image signal is updated, setting of the image processing is updated such that substantially the same image as the image displayed on the display unit by the first image signal before being updated is displayed on the display unit.

* * * * *